(12) United States Patent
Callahan et al.

(10) Patent No.: US 6,786,928 B2
(45) Date of Patent: Sep. 7, 2004

(54) SMALL INCISION LENS

(75) Inventors: Wayne B. Callahan, Abingdon, VA (US); Jeffery S. Callahan, Blountville, TN (US)

(73) Assignee: ThinOptX, Inc., Abingdon, VA (US)

( * ) Notice: Subject to any disclaimer, the term of this patent is extended or adjusted under 35 U.S.C. 154(b) by 0 days.

(21) Appl. No.: 10/195,953

(22) Filed: Jul. 16, 2002

(65) Prior Publication Data

US 2003/0065387 A1 Apr. 3, 2003

Related U.S. Application Data

(60) Continuation-in-part of application No. 09/441,425, filed on Nov. 16, 1999, now Pat. No. 6,488,707, which is a division of application No. 08/914,767, filed on Aug. 20, 1997, now Pat. No. 6,096,077

(60) Provisional application No. 60/305,811, filed on Jul. 17, 2001, provisional application No. 60/344,615, filed on Dec. 31, 2001, and provisional application No. 60/385,006, filed on May 31, 2002.

(51) Int. Cl.$^7$ .................................................. A61F 2/16
(52) U.S. Cl. ..................... 623/6.18; 623/6.25; 623/6.27
(58) Field of Search ............................. 623/5.14, 5.15, 623/6.18, 6.25, 6.27, 6.28, 6.29, 6.3, 6.31, 6.54, 5.16, 6.39, 6.4, 6.43, 6.44, 6.56; 351/160 R

(56) References Cited

U.S. PATENT DOCUMENTS

| | | |
|---|---|---|
| 4,102,567 A | 7/1978 | Cuffe et al. |
| 4,215,440 A | 8/1980 | Worst |
| 4,254,509 A | 3/1981 | Tennant |
| 4,573,998 A | 3/1986 | Mazzocco |
| 4,585,456 A | 4/1986 | Blackmore |
| 4,608,049 A | 8/1986 | Kelman |
| 4,624,669 A | 11/1986 | Grendahl |
| 4,655,775 A | 4/1987 | Clasby, III |

(List continued on next page.)

FOREIGN PATENT DOCUMENTS

JP 401015042 A * 1/1989

OTHER PUBLICATIONS

*Hackh's Chemical Dictionary*, 4$^{th}$ Edition (1969) p. 232, 611, McGraw-Hill Book Co., New York City.

Adrian Glasser, et al., *Presbyopia: A View*, emedicine.com (Aug. 20, 2001) 2:1-15, eMedicine Journal.

Primary Examiner—Paul B. Prebilic
(74) Attorney, Agent, or Firm—Waddey & Patterson; Douglas W. Schelling

(57) ABSTRACT

This patent represents a deformable artificial intraocular lens for implantation into the human eye. The lens is used for implantation after cataract surgery. The lens optic consists of one smooth optical surface. The second optical surface is a series of annular concentric rings. The rings allow the lens to have extremely thin edges, which reduce glare, halos, and distortion. The extremely thin lens optic along with the thin haptic can be rolled, folded, or squeezed to pass through a small incision (<1.5 millimeters) in the cornea or sclera of the human eye. This lens represents a breakthrough in removal of mass from the lens. The ultra thin lens and haptic design allows the lens to move in the eye providing accommodation for the patient. The lens and haptic design reduces the radial forces on the eye to the point where the naturally occurring pressures in the eye move the lens thus providing accommodation. In all current lens designs the haptics apply enough radial force to prevent the natural forces in the eye from moving the lens. The ultra thin lens and haptic design allows the lens to move in the eye providing accommodation for the patient.

34 Claims, 13 Drawing Sheets

U.S. PATENT DOCUMENTS

| | | | |
|---|---|---|---|
| 4,769,035 A | 9/1988 | Kelman | |
| 4,795,462 A | 1/1989 | Grendahl | |
| 4,816,032 A | 3/1989 | Hetland | |
| 4,828,558 A | 5/1989 | Kelman | 623/6 |
| 4,834,750 A | 5/1989 | Gupta | |
| 4,863,462 A * | 9/1989 | Fedorov et al. | 623/6.44 |
| 4,919,130 A * | 4/1990 | Stoy et al. | 606/107 |
| 4,932,970 A | 6/1990 | Portney | 623/6.2 |
| 4,950,290 A | 8/1990 | Kamerling | |
| 4,994,080 A | 2/1991 | Shepard | |
| 4,995,714 A | 2/1991 | Cohen | 351/161 |
| 5,002,568 A | 3/1991 | Katzen | |
| 5,076,684 A | 12/1991 | Simpson et al. | |
| 5,098,444 A | 3/1992 | Feaster | |
| 5,100,226 A | 3/1992 | Freeman | |
| 5,166,711 A | 11/1992 | Portney | |
| 5,178,636 A | 1/1993 | Silberman | 623/6 |
| 5,192,319 A | 3/1993 | Worst | |
| 5,229,797 A | 7/1993 | Futhey et al. | |
| 5,236,452 A * | 8/1993 | Nordan | 623/6.24 |
| 5,258,025 A | 11/1993 | Fedorov et al. | |
| 5,476,512 A * | 12/1995 | Sarfarazi | 623/6.39 |
| 5,476,514 A | 12/1995 | Cumming | |
| 5,480,428 A | 1/1996 | Fedorov et al. | |
| 5,522,890 A | 6/1996 | Nakajima et al. | |
| 5,549,670 A | 8/1996 | Young et al. | |
| 6,096,077 A | 8/2000 | Callahan et al. | |
| 6,152,958 A | 11/2000 | Nordan | 623/6.25 |
| 6,197,059 B1 | 3/2001 | Cumming | |
| 6,623,522 B2 * | 9/2003 | Nigam | 623/5.13 |
| 2002/0161437 A1 | 10/2002 | Zhou et al. | |

* cited by examiner

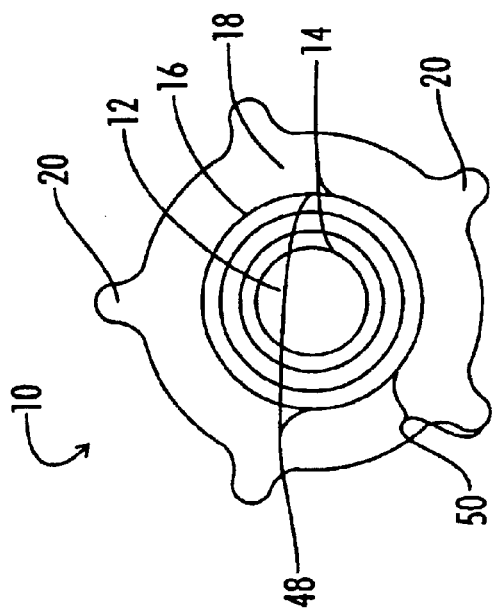
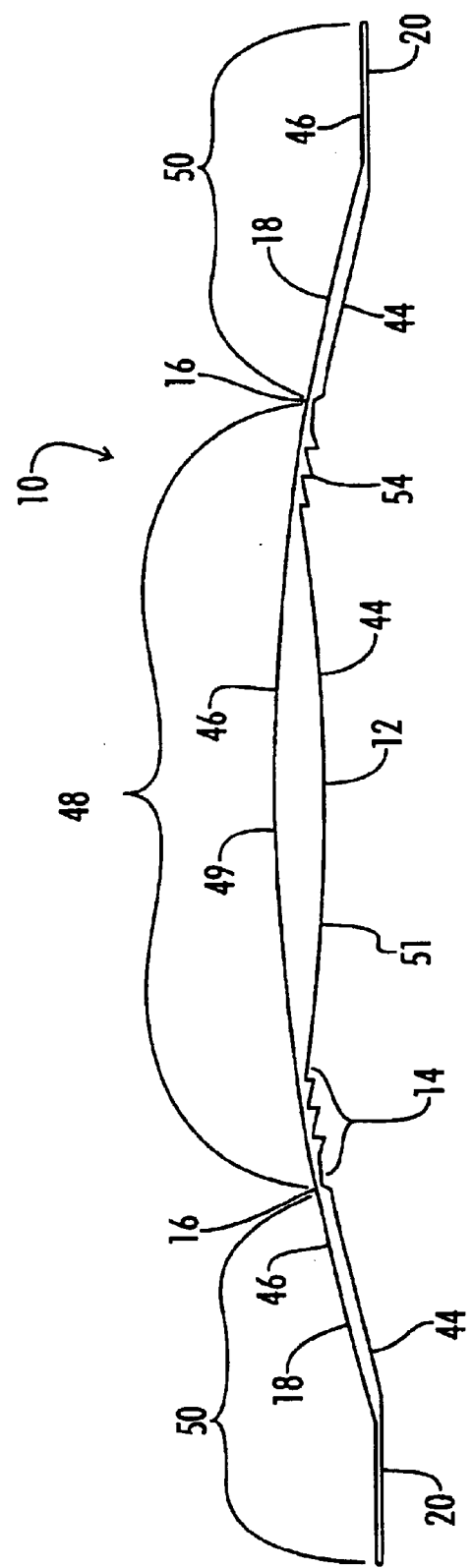
FIG. 1
FIG. 2

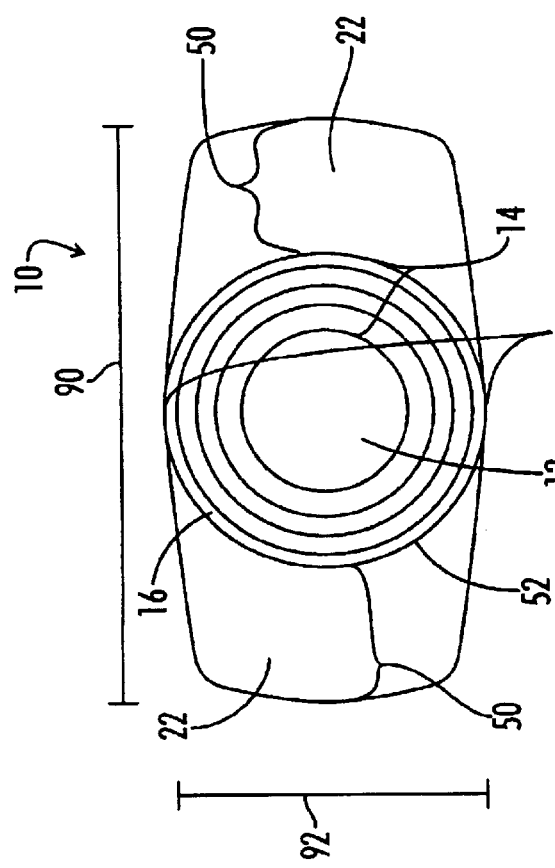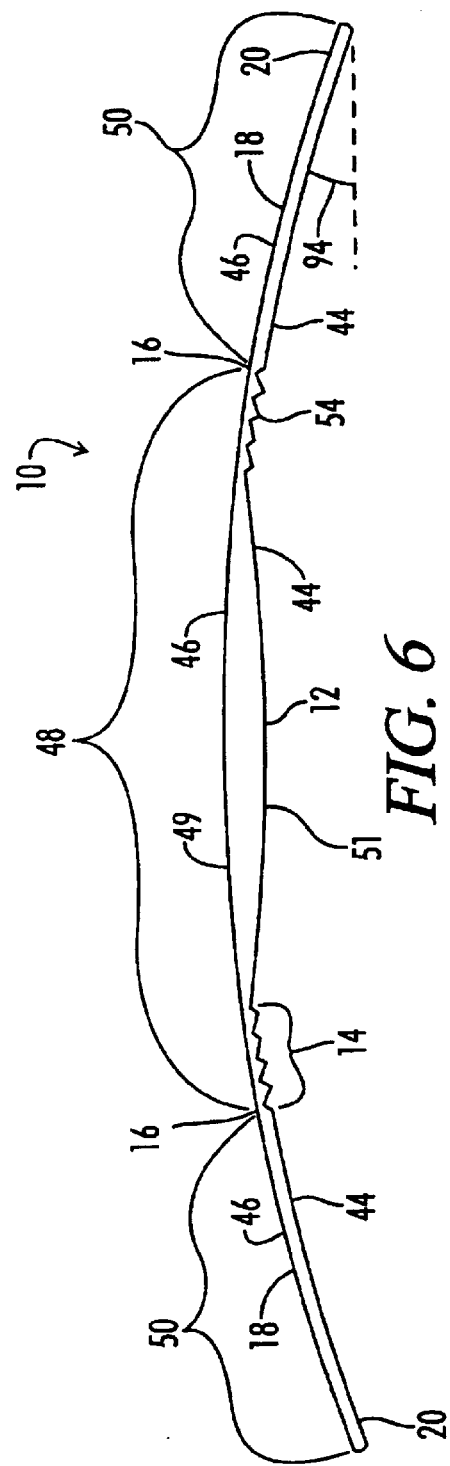

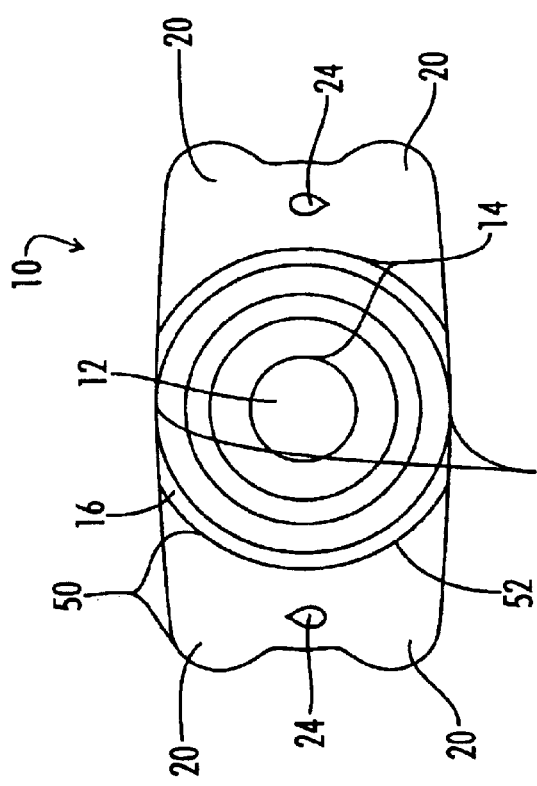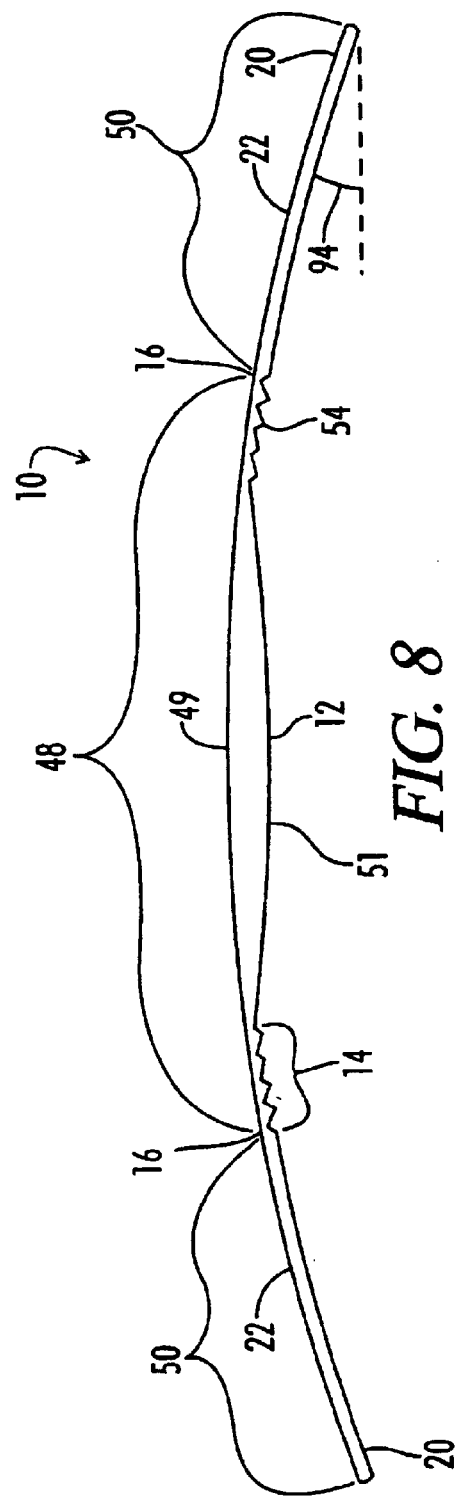
*FIG. 7*
*FIG. 8*

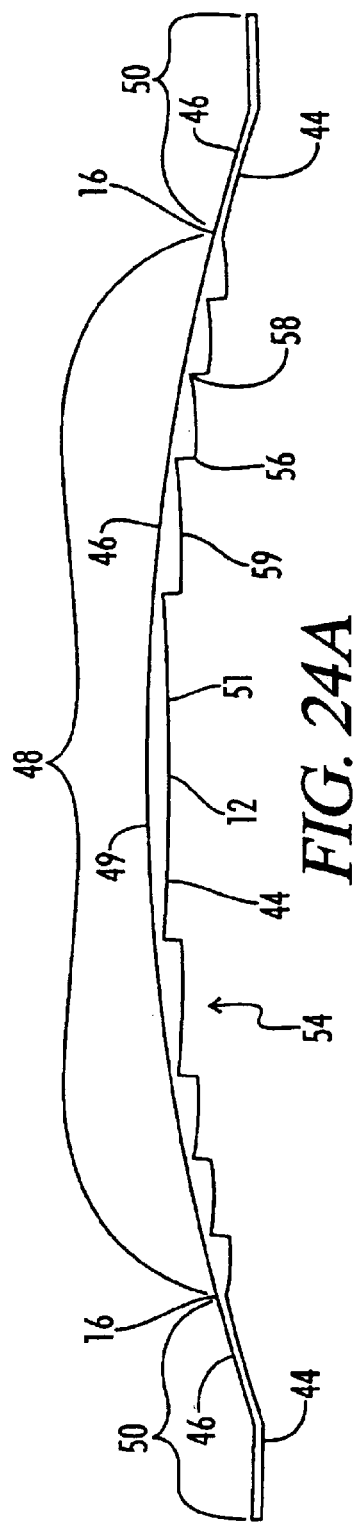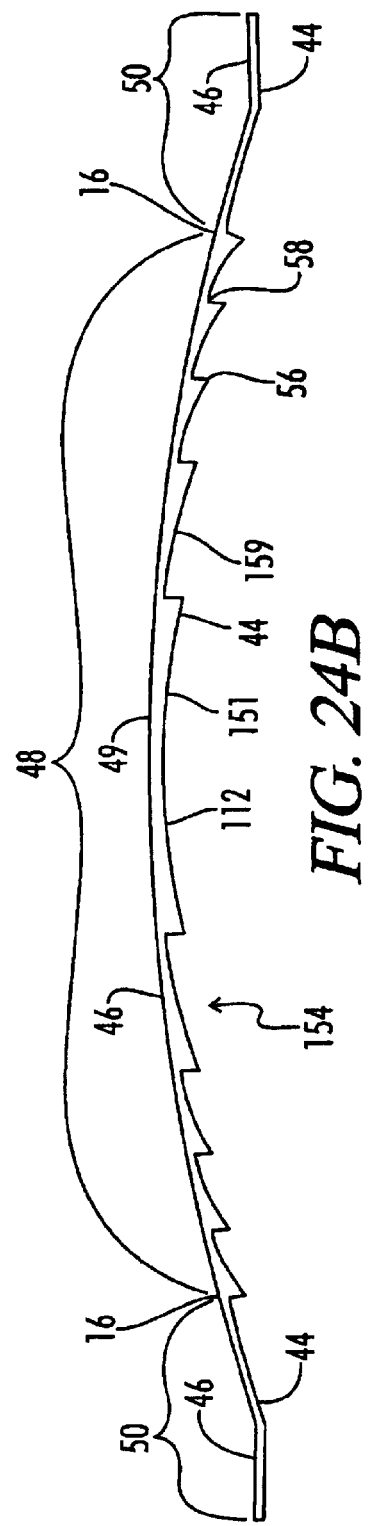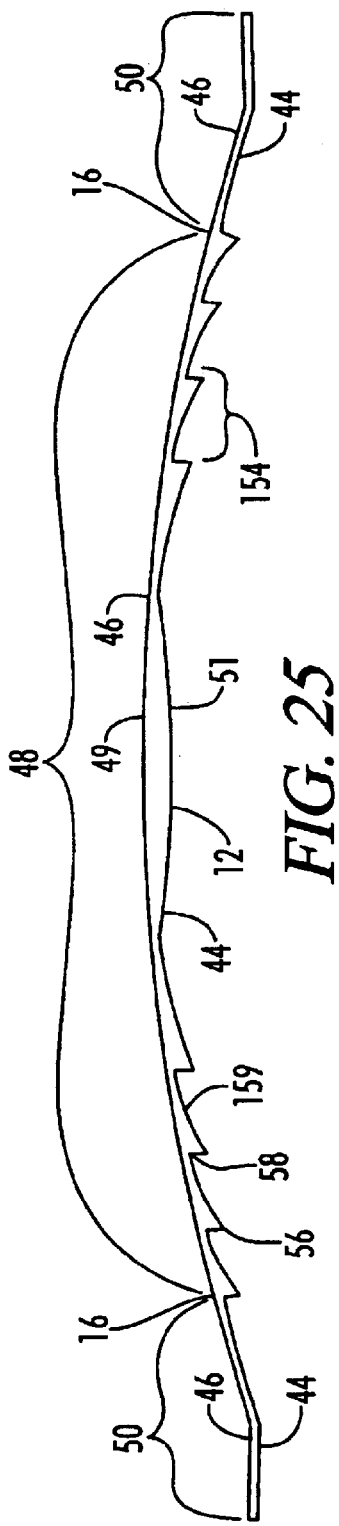

SMALL INCISION LENS

This application claims benefit of co-pending U.S. Provisional Patent Application Serial No. 60/305,811 filed Jul. 17, 2001, entitled "Small Incision Cataract Lens" which is hereby incorporated by reference, and U.S. Provisional Patent Application Serial No. 60/344,615 filed Dec. 31, 2001, entitled "Intraocular Lens" which is hereby incorporated by reference, and U.S. Provisional Patent Application Serial No. 60/385,006 filed May 31, 2002, entitled "Small Incision Cataract Lens and Methods of Use Thereof" which is hereby incorporated by reference, and this application also is a continuation-in-part application of U.S. patent application Ser. No. 09/441,425 filed Nov. 16, 1999, now U.S. Pat. No. 6,488,707, entitled "Method of Implanting a Deformable Intraocular Corrective Lens," which is hereby incorporated by reference, which is a divisional application of U.S. patent application Ser. No. 08/914,767 filed Aug. 20, 1997, now U.S. Pat. No. 6,096,077, entitled "Deformable Intraocular Corrective Lens" which is hereby incorporated by reference.

Be it known that we, Wayne B. Callahan, a citizen of The United States, residing at 18952 Middle Drive, Abingdon, Va. 24211; and Jeffery S. Callahan, a citizen of The United States, residing at 104 Eagleview Dr. Blountville, Tenn. 37617 have invented a new and useful "Small Incision Lens."

FIELD OF THE INVENTION

The present invention relates generally to the area of intraocular lens and use thereof to correct visual problems. More particularly, this invention provides a lens and method of use thereof for the correction of a lack of accommodation. The lens can be inserted into a human eye through a 1.5 millimeter or smaller incision.

BACKGROUND OF THE INVENTION

Doctors trained in ophthalmology routinely surgically extract cataract-impaired natural crystalline lenses from patients' eyes and subsequently implant artificial lenses to prevent blindness.

Using an intraocular lens for correction of visual problems is currently problematic. In order to insert an intraocular lens, an incision is made through the cornea or sclera. The new lens is passed through the incision into the anterior chamber of the eye. The inserted lens is then positioned over the pupil and anchored either anteriorly to or posteriorly from the iris, or other structure of the eye. Unfortunately, the making of the incision causes astigmatism of the cornea.

Alternative lens materials are also currently used for the replacements of the natural lenses of cataract patients. One such alternative lens material is an acrylic that has a lower molecular weight than PMMA. This lower-weight acrylic lens is softer than PMMA so it can be folded in a U-shape. However, if not handled very carefully, the lower-weight acrylic will crease, rendering it unusable. In addition, the material is soft enough to adhere to itself if it is rolled or folded far enough to allow overlapping.

Another alternative lens material is silicone, the same material that is used in breast implants. The silicone collects protein in some patients, giving a yellow appearance and reducing the passage of light. The protein can become so dense as to create the appearance of a secondary cataract, significantly reducing the patient's ability to see. This is usually a lesser concern for cataract patient, when compared to the blindness, which would result from the cataract. Also, most cataract patients tend to be elderly so the protein build-up might not advance too far during their lifetimes. For some cataract patients, though, the protein build-up necessitates that the silicone lens be removed and replaced. Because of the problems associated with protein build-up, silicone cannot be used to make long-term intraocular lenses for implantation into younger persons.

Two inventions for a deformable intraocular lens are set forth in U.S. Pat. No. 4,573,998 issued March 1986, to Mazzocco; and U.S. Pat. No. 5,522,890 issued June 1996, to Nakajima et al. These inventions employ a lens made of a molded elastic material. They do not suggest the use of PMMA, nor do they suggest rolling an extremely thin lens to allow an incision size considerably smaller than required for the folded lens.

Other inventions generally related to the art of optical lenses include: U.S. Pat. No. 4,254,509 issued March 1981, to Tennant (Accommodating Intraocular Implant); U.S. Pat. No. 4,585,456 issued April 1986, to Blackmore (Corrective Lens for the Natural Lens of the Eye); U.S. Pat. No. 4,655,775 issued April 1987, to Clasby (Intraocular Lens with Ridges); U.S. Pat. No. 4,769,035 issued September 1988, to Kelman (Artificial Lens and the Method for Implanting Such Lens); U.S. Pat. No. 4,795,462 issued January 1989, to Grendahl (Cylindrically Segmented Zone of Focus Artificial Lens); U.S. Pat. No. 4,816,032 issued March 1989, to Hetland (Arrangement in an Intraocular Anterior Chamber Lens); U.S. Pat. No. 4,950,290 issued August 1990, to Kamerling (Posterior Chamber Intraocular Lens); U.S. Pat. No. 4,994,080 issued February 1991, to Shepard (Optical Lens Having at Least One Stenopaeic Opening Located in the Central Area Thereof); U.S. Pat. No. 5,076,684 issued December 1991, to Simpson et al. (Multi-Focal Diffractive Ophthalmic Lenses); U.S. Pat. No. 5,098,444 issued March 1992, to Feaster (Epiphakic Intraocular Lens and Process of Implantation); U.S. Pat. No. 5,166,711 issued November 1992, to Portney (Multifocal Ophthalmic Lens); U.S. Pat. No. 5,229,797 issued July 1993, to Futhey et al. (Multifocal Diffractive Ophthalmic Lenses); U.S. Pat. No. 5,258,025 issued November 1993, to Fedorov et al. (Corrective Intraocular Lens); U.S. Pat. No. 5,480,428 issued January 1996, to Fedorov et al. (Corrective Intraocular Lens). None of these inventions solves the above-disclosed problems associated with currently known deformable intraocular lenses.

SUMMARY OF THE INVENTION

A deformable artificial intraocular lens for implantation into the human eye is disclosed herein. The lens is used for the correction of myopia, hyperopia, presbyopia, astigmatism, or for implantation after cataract surgery. The lens optic consists of one smooth optical surface. The second optical surface is a series of annular concentric rings. The rings allow the lens to have extremely thin edges, which reduce glare, halos, and distortion. The rings also allow the overall thickness of the lens to be significantly thinner than a standard lens. This allows the lens to be inserted through an incision of 1.5 millimeters or smaller. A standard lens currently passes through an incision that is approximately 3 millimeters. The rings on the second surface are adjusted to reduce the spherical aberrations from the design of the first surface optic being spherical. Such a thin lens also reduces coma, and other Third Order Theory Aberrations (Fundamentals of Optics, Francis A. Jenkins and Harvey E. White, Fourth Edition, Copyright by McGraw-Hill, Inc. 1950 renewed in 1957 and 1976, page 151 through 160), which also create halos and glare.

Also disclosed herein is a method of correcting a loss of accommodation comprising removing a natural crystalline lens from the eye and inserting an intraocular lens in the eye. In certain embodiments, the method further comprises unrolling the intraocular lens so that a haptic footplate contacts the natural lens sac or the ciliary body in order to hold the intraocular lens in position and produce a minimum radial force on the eye.

Accordingly, one aspect of the present invention is an intraocular lens, comprising an optical portion having a first optical surface, wherein the optical portion is constructed of a material which is biologically compatible with a tissue of an eye, the optical portion having a predetermined maximum thickness under which the material may be rolled without exceeding the elastic limit of the material, said optical portion having a predetermined minimum thickness above which the material retains said normal shape, wherein the intraocular lens is deformed for passage through an incision having a length smaller than about 1.5 millimeters so that the intraocular lens is placed into the eye; the optical portion having a second optical surface, wherein the second optical surface comprises a central disk which is radially surrounded by a series of annular rings, the central disk and the series of annular rings forming a series of radial steps along the second optical surface so that a focal length from an annular ring is adjusted to focus at a same point as a prime meridian of the lens, wherein the second optical surface and the first optical surface have a minimum separation of 0.025 mm and a maximum separation of 0.45 mm; and an anchoring portion attached to the optical portion, wherein the anchoring portion is constructed of a material which is biologically compatible with a tissue of an eye, wherein the anchoring portion is capable of biasing against a support structure of the eye. In certain embodiments, the second optical surface and the first optical surface have a minimum separation of 0.025 mm and a maximum separation of 0.065 mm.

Another aspect of the present invention is that the first optical surface and the second optical surface are of a predetermined convexity for obtaining a particular focusing power. In certain embodiments, the first optical surface and the second optical surface are of a predetermined concavity for obtaining a particular focusing power. In still other embodiments, the first optical surface is of a predetermined convexity for obtaining a particular focusing power, and the second optical surface is of a predetermined concavity for obtaining a particular focusing power. In other embodiments, the first optical surface is of a predetermined concavity for obtaining a particular focusing power, and wherein the second optical surface is of a predetermined convexity for obtaining a particular focusing power. In yet another embodiment of the present invention, the first surface is of a predetermined concavity for obtaining a particular focusing power, and wherein the second optical surface is of a predetermined concavity for obtaining a particular focusing power.

Another aspect of the present invention is the ultra thinness of the anchoring portion. In certain embodiments, the anchoring portion has a thickness of about 10 microns to about 100 microns. In other embodiments, the anchoring portion has a maximum thickness of about 100 microns. In other embodiments, the anchoring portion comprises a plurality of anchoring footplates or a plate haptic.

Still another aspect of the present invention is a lens constructed of an acrylic material, a hydrophilic acrylic material, a hydrophobic acrylic material, any semi-rigid material having a thickness that is less than the elastic limit of the semi-rigid material, hydrogel, polymethylmethacrylate, or a material having an index of refraction from about 1.4 to about 2.0.

Another aspect of the claimed invention is the method of using the intraocular lens. In certain embodiments, a method of correcting a visual defect is provided. The method includes providing an intraocular lens as described herein, warming the intraocular lens to a temperature from about 90 degrees F. to about 150 degrees F., making an incision having a length of less than 1.5 mm in an eye, removing a natural lens of the eye, deforming the intraocular lens, cooling the intraocular lens to a temperature from about 60 degrees F. to about 80 degrees F., inserting the intraocular lens into the eye through the incision, contacting the intraocular lens with an intraocular fluid within the eye so that the intraocular lens warms and unrolls, and positioning the intraocular lens so that the anchoring portion biases against the support structure of the eye. In certain embodiments, positioning the intraocular lens further comprises biasing the anchoring portion against an anterior and posterior capsule structure, wherein biasing produces a minimum radial force on the eye. In still other embodiments, positioning the intraocular lens further comprises biasing the anchoring portion against zonules and a posterior iris, wherein biasing produces a minimum radial force on the eye, so that the anchoring portion of the intraocular lens is held in a fixed position.

Another aspect of the present invention is deforming the intraocular lens. In certain embodiments, the lens is rolled around a rod. In other embodiments, the lens is rolled around itself. In certain embodiments, the incision is repaired.

Once rolled and passed through the cornea, the implanted intraocular lens may be placed in a position. In certain embodiments, the implanted lens may be positioned anterior to the iris, in the anterior chamber of the eye. If this position is chosen, the haptic edge of each of the haptic fingers will be biased against the anterior chamber angle 31, the angle formed by the cornea and root of the iris and behind the trabeculum. Once positioned and allowed to unroll, the implanted lens will return to its original shape.

Alternatively, the implanted lens may be positioned posteriorly from the iris, and rest in front of the capsule of the natural lens of the eye. If this position is chosen, the haptic edge of each of the haptic fingers will be biased against the zonules and posterior iris surface or ciliary sulcus. The implanted lens is able to be placed posteriorly from the iris because of the thinness of the implanted lens.

The lens may also be implanted into the capsule that contained the natural lens after removal of the natural lens. One reason for the removal of the natural lens is a clouding of the natural lens, cataract. A second reason for removing the natural lens is to allow placement of an intraocular lens for cases of poor visions caused by extreme cases of myopia or hyperopia.

Another aspect of the present invention is using the lens disclosed herein to correct visualization of glare, halos, to reduce coma, and to correct spherical aberrations. In certain embodiments, the lens moves in order to correct a lack of accommodation. In certain embodiments, the intraocular lens moves toward an anterior surface of the eye when a ciliary muscle in the eye relaxes While positioning the intraocular lens, in certain embodiments, the anchoring portion is curled toward the anterior surface of the capsule structure. In other embodiments, the anchoring portion is curled toward the posterior surface of the capsule structure.

Another aspect of the invention is a lens having a marker to indicate the direction of the lens.

The present invention is a deformable intraocular lens that may be rolled or folded for insertion into the human eye to correct common vision problems or for the replacement of the natural lens after cataract surgery. The lens is deformable because all portions of the lens are manufactured to a thickness, which is within a predetermined range of thicknesses. More particularly, at the first end of the range, the thickness of the lens is less than a maximum material thickness, the threshold under which the material is flexible. At the second end of the range, the thickness of the lens is also greater than a minimum material thickness, the threshold above which the lens material will retain its pre-flexed shape subsequent to flexing. The novel design also enables the deformable lens to possess any desired convexity or concavity, which would be required for correction of visual problems. Of course, the deformable lens of the present invention may also be constructed from any other biologically compatible material that can be manufactured thinner than a pre-determined maximum material thickness to be rolled or folded for passage through a small incision in the cornea or sclera.

An anchoring portion is attached to the optical portion to securely position the deformable intraocular contact lens, anteriorly to the natural lens of the eye. In certain embodiments, the lens also has a non-optical transition area interconnecting the anchoring means to the optical portion of the lens. The transition area has a thickness of approximately 0.025 mm. The anchoring means comprises a pair of haptic fingers extending from the transition area and circumvolving the optical lens. The thickness of the haptic fingers is preselected to provide the optimal combination of strength and flexibility. The outer circumference of the haptic finger comprises the haptic edge. The haptic edge of the implanted lens is biased against the intraocular tissues. The thickness of the haptic edge is preselected to provide minimal stress to the eye tissues.

BRIEF DESCRIPTION OF THE DRAWINGS

FIG. 1 is a plan view of the lens 10 with an ultra thin optic and haptic. Also shown are the central disk 12, the series of annular rings 14, the thin edge of the optical portion 16, an anchoring portion 50, in this case a haptic 18, and an anchoring footplate 20, also called a haptic footplate. The anchoring portion of the lens is thinner than the optical portion. In this figure, there are five footplates. The lens 10 is constructed of material that is biologically compatible with the tissue of the eye. As shown, the haptic 18 circumvolves, or surrounds, the optical portion 48 of the lens 10. Each anchoring footplate 20 biases against a support structure that is used for attachment to the eye.

FIG. 2 is a sectional view of a lens 10 with a convex first optical surface 49. This view illustrates the ultra thinness of the lens 10 including the anchoring portion 50. In this figure the haptic 18 has an angle greater than zero.

FIG. 5 is a plan view of a lens 10 with a plate haptic 22. This figure illustrates one of the different types of ultra thin haptics that can be coupled with the thin optic design to form lenses that will fit through an incision that is smaller than 1.5 millimeters. The width 92 can vary from about 5 millimeters to about 8 millimeters. The length 90 can vary from about 10 millimeters to about 14 millimeters.

FIG. 6 is a sectional view of the plate style lens. Although an angle 94 is shown, and represents, an angle of +10 degrees, the angle 94 can vary from about +10 degrees to about 0 degrees. The lens can be implanted with the smooth, first surface 46 facing anteriorly or posteriorly. For refractive lenses the continuous surface is normally implanted facing anteriorly toward the cornea 96. When used as a cataract lens the lens is implanted with the continuous surface positioned posteriorly. Therefore, when the haptic is angled the angle is positive when the continuous surface is facing anteriorly and negative when the continuous surface is facing posteriorly. This figure also shows a biconvex lens, having a convex first optical surface 49 and a convex second optical surface 51.

FIG. 7 is a modified plate lens wherein the anchoring portion 50 is displayed as ultra thin plate haptic. This haptic can be used with the thin optic design shown in FIGS. 2 and 3. The markers 24 in the lens haptic are used for positioning and are well known in the art. The markers 24, also called teardrop openings, in the haptic indicate when the lens is in the correct position. In this figure, the markers 24 point clockwise. In other embodiments, the markers 24 point counterclockwise. Accordingly, the markers 24 indicate orientation.

FIG. 8 is a cross section of the modified ultra thin plate haptic 22 lens 10 used in the preferred embodiment.

FIG. 24A shows a cross section view of an embodiment of the invention in which the first surface 46 is convex and the surfaces of the central disk 12 and each of the annular rings 54 are convex.

FIG. 24B shows a cross section view of an embodiment of the invention in which the first optical surface 49 is convex and the surfaces of the central disk 112 and each of the annular rings 154 are concave.

FIG. 25 shows a cross section view of an embodiment of the invention in which the first optical surface 49 of the optical portion 48 and the surface of the central disk 12 are convex. The outer surface 159 of each annular ring 154 is concave.

DESCRIPTION OF THE PREFERRED EMBODIMENTS

Figure 3:
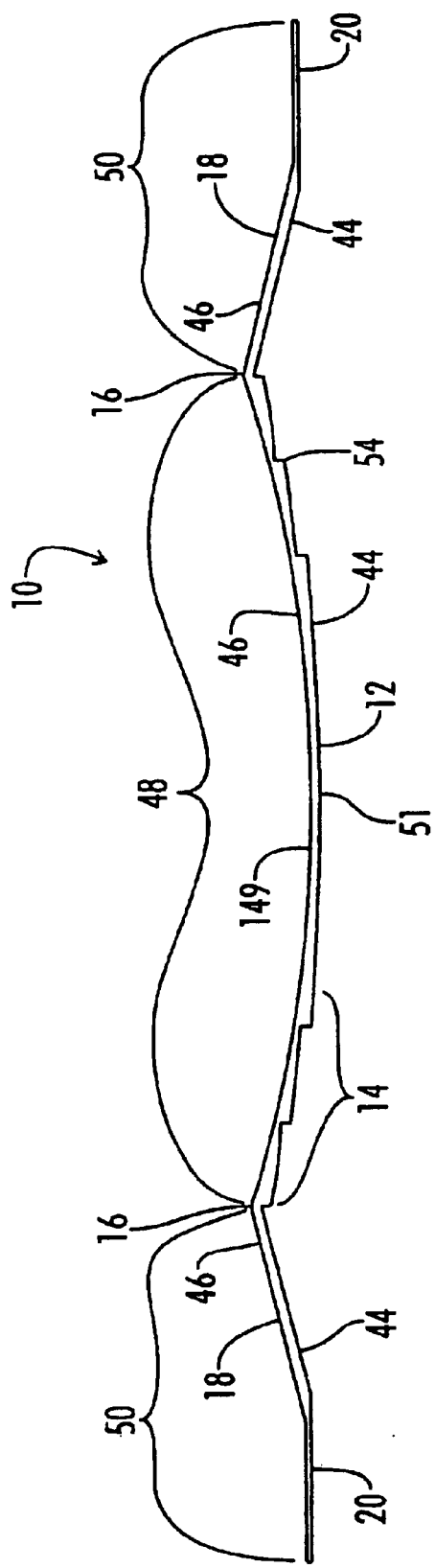
FIG. 3 is a sectional view of a lens 10 with concave first optical surface 149. Again the view illustrates the ultra thinness of the lens 10.
Figure 4:
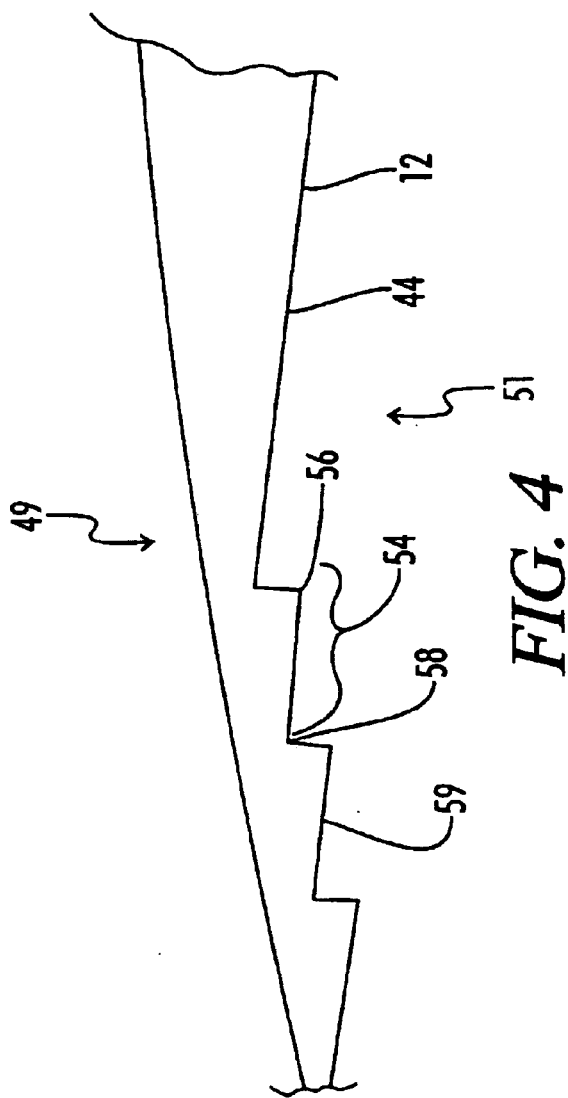
FIG. 4 is a sectional view of a lens 10 showing the detail of the series of annular rings 14, including each individual annular ring 54, the first section of the annular ring 56, and the second section of the annular ring 58.
Figure 9:
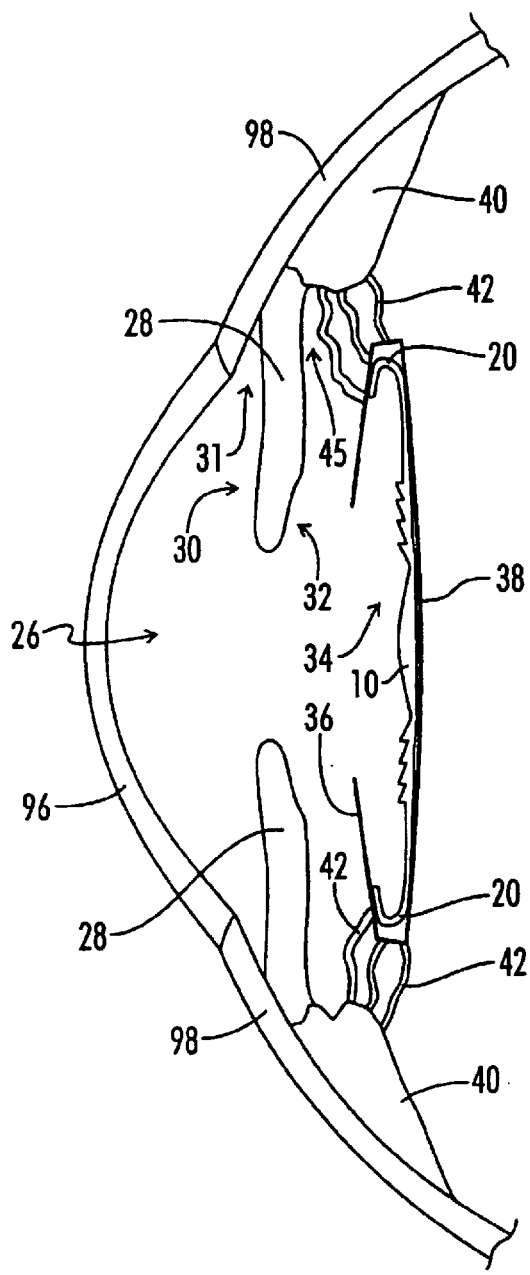
FIG. 9 shows a lens 10 in an aphakic eye with the thinner section of the haptic 20 rolling in the capsule 34. The lens 10 is positioned against the posterior surface 38 of the capsule 34 and held in position by the haptic footplates 20 resting against the posterior surface 38 of the capsule 34 and the anterior surface 36 of the capsule 34. With time, the anterior and posterior capsules grow together and the lens is further fixated in the eye since the tissue from the anterior and posterior segment grow together through the positioning markers 24, as shown in FIG. 7.

Many visual problems can only be corrected by removing the natural lens from the eye and replacing it with an intraocular lens. Although such lens replacement will enhance the visual ability of the patient, the lenses described in the prior art often create secondary visual problems. For example, many patients have difficulty driving at night due to glare, halos and rings from on coming automobile headlamps, taillights and street lamps. The secondary visual problems often come from Third Order Aberrations (Fundamentals of Optics by Francis A. Jenkins and Harvey E. White, copyright renewed 1965, Library of congress ISBNO-07-0323330-5, pages 151 and 152), which, in general, are the sum of the light ray deviations from the path as to allow all light rays across the lens surface to focus at the focal point of the prime meridian. The Gaussan formulas errors increase as the distance from the prime meridian increases. The formulas also assume an infinitesimally thin lens, which would eliminate coma and other aberrations. The errors associated with the Gaussan formulas are expressed in terms of five sums called the Seidel sums. The Seidel sums include spherical aberrations, coma, distortions, astigmatism and curvature of field.

The intraocular lens and methods of use thereof, which are described herein, resolve much of the secondary visual problems created by Third Order Aberrations that commonly occur. Briefly, the intraocular lens 10 has a series of annular rings 14 and a maximum thickness which allow the lens 10 to be rolled, squeezed, or otherwise compressed for insertion through a corneal incision, or incision of sclera, of less than 1.5 millimeters. Each annular ring 54 has two sides arranged as shown in FIGS. 2, 3, 4, 6, 8, 18, 22, 23, and 24. Additionally, the thin construction of the lens 10 and haptic 18 allows the lens 10 to move within the location of insertion in order to correct a lack of accommodation.

As used herein, "aphakic eye" means an eye with the natural lens removed.

As used herein, "phakic eye" means an eye with the natural lens still in place.

As used herein, "support structure of the eye," means a structure of the eye where a lens can be placed. The following are examples of support structures. These examples do not exclude other support structures that are not mentioned. The anterior angle 31 of the anterior chamber 26 of the eye, as shown in FIGS. 9–13, is the area at the far end of the cornea 96 and iris 28 where the two structures come together. Another example of a support structure includes the ciliary cavity 45, also shown in FIGS. 9–13, which is defined as the area where the zonules 42 attach to the ciliary body 40 and the posterior surface of the iris 32. The lens can also be placed in the capsule 34 remaining after removing the natural lens. When the lens is placed in the capsule 34 left after removing the natural lens, the anchoring portion rests against the posterior surface 38 of the capsule 34 and the anterior surface 36 of the capsule 34.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, the preferred methods and materials are described below. All publications, patent applications, patents, and other references mentioned herein are incorporated by reference in their entirety. Unless otherwise indicated, materials, methods, and examples described herein are illustrative only and not intended to be limiting.

Until the development of the current invention, the existence of a truly thin lens was consider theoretical (Optical Engineering Fundamentals by Bruce H. Walker, and edited by Donald C. O'Shea, George Institute of Technology. Published by SPIE Optical Engineering Press, A Publication of SPIE—The International Society of Optical Engineering, Bellingham, Washington USA). On page 57, the aforementioned text states, "A thin lens is a lens whose thickness is assumed to be zero and therefore is negligible. The thin lens is a design tool, used to simulate a real lens during the preliminary stages of optical system design and analysis." Later in the same paragraph the text states "By assuming a lens form where the thickness is zero, the formulas used to calculate object and image relationships are greatly simplified. The drawback to the thin-lens approach is that it is not possible to determine image quality without including the actual lens thickness (and other lens data) in the calculations. As a result, while it is possible to establish many valuable facts about an optical system through the application of the thin-lens theory and formulas, the ultimate quality of the image can, at best, only be estimated."

The current invention is based on a lens that is thin enough to approach the theoretical zero thickness, yet has enough thickness to support the optical structure. This allows the thickness of the lens to be ignored in calculations. Thus, the present invention discloses a lens that approaches a theoretically perfect lens.

The Gaussan lens theories (Fundamentals of Optics, Jenkins and White, page 48) assume the power of a lens is equal to the difference between the indexes of refraction of the lens material and the media in which the lens is surrounded divided by the radius of curvature of the lens surface.

Figure 23:
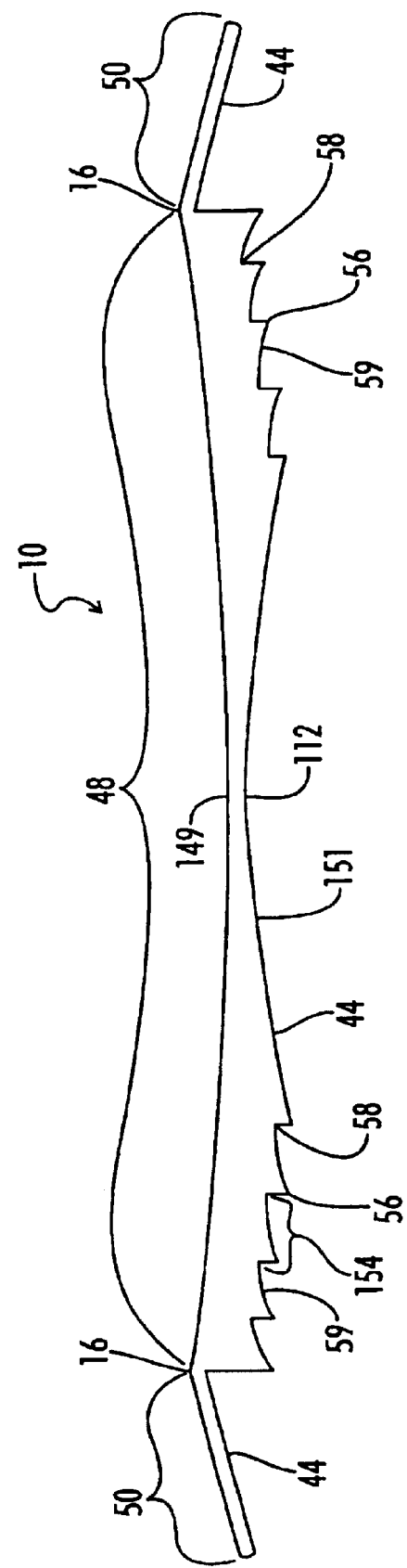
FIG. 23 shows a cross section view of an embodiment of the invention in which the first optical surface 149 and the surfaces of the central disk 112 and each of the annular rings 154 are concave.

As seen in FIG. 1, the present invention discloses a lens 10 having an optical portion 48 and an anchoring portion 50. The optical portion 48 has a first optical surface 49 and a second optical surface 51. In certain embodiments, the optical portion 48 of the lens 10 has a biconvex structure, as best seen in FIGS. 2, 6, 8, 22, and 24A. In other embodiments, the optical portion 48 of the lens 10 has a biconcave structure, as seen in FIG. 23. In still other embodiments, the optical portion 48 has a convex first optical surface 49 and a concave second optical surface 151, as shown in FIG. 24B. In certain embodiments, note that a convex second is optical surface 51, further comprises a convex central disk 12 and annular rings 54 having convex outer surfaces 59, as shown in FIG. 24A. In other embodiments, a concave second optical surface 151, further comprises a concave central disk 112 and annular rings 54 having concave outer surfaces 159, as shown in FIG. 24B. The predetermined convexity or concavity of the outer surface 59 of the annular ring 54 adjusts the focal length of the annular ring to focus at a same point as a prime meridian of the lens. In other embodiments, the optical portion 48 has a concave first optical surface 149 and a convex second optical surface 51, as shown in FIG. 3. Reference number 49 represents a first optical surface having a convex shape. Reference number 149 represents a first optical surface having a concave shape. Claim language referencing the first optical surface could apply to either. Reference number 51 represents a second optical surface having a convex shape. Reference number 151 represents a second optical surface having a concave shape. Claim language referencing the second optical surface could apply to either.

In another embodiment, as shown in FIG. 25, the first optical surface 49 of the optical portion 48 and the central disk 12 are of a predetermined convexity for obtaining a particular focusing power and the outer surface 159 of each annular ring 154 is of a predetermined concavity. The shape of the outer surface 159 adjusts the focal length from the annular ring 154 to a same point as a prime meridian of the lens 10.

In certain embodiments, the intraocular lens 10 has a first surface 46 that is convex. Generally, as seen in FIGS. 1–8 and 22–24, the second surface 44 of the lens 10 comprises a planar, central disk 12 which is surrounded by a series of concentric, planar, annular rings 54 of increasing diameter. The annular rings 54 are parallel to each other and to the central disk. The central disk 12 and annular rings 54 are also perpendicular to a radial axis passing though the apex of the first surface. In combination, the central disk 12 and the series of annular rings 14 form a series of steps extending radially from the disk across the second surface 44 to maintain a close proximity to the first surface 46.

In still other embodiments, the thickness of the lens between the central disk of the second surface and the apex of the first surface must be less than a predetermined maximum thickness. The predetermined maximum thickness is the thickness under which the material may be rolled or folded without exceeding the elastic limit of the selected lens material.

In still other embodiments, the thickness of the lens at the periphery of the central disk must be greater than a predetermined minimum thickness. The predetermined minimum thickness is the thickness above which the lens material will retain its pre-flexed shape subsequent to flexing. The minimum thickness is determined by the manufacturing process and the strength of the lens material.

The radial width of the central disk 12 of the second surface 44 also falls within a predetermined range. The thicker the lens is at its apex, the farther the radial width may extend before the periphery of the central disk 12 approaches the predetermined minimum thickness. The specific range of radial widths is determined by both the convexity of the first surface and the thickness of the lens at its apex.

Similar to the central disk 12, the thickness between the first surface 46 and the second surface 44 of the lens 10 at the internal diameter of each annular ring, or most distal point, should be less than or equal to the predetermined maximum thickness. The thickness between the first surface and the second surface of the lens at the external diameter of each annular ring, or closest point, should be greater than or equal to the predetermined minimum thickness. The radial width of the annular rings will be within a predetermined range of lengths, which is determined by the convexity of the first surface and the thickness of the lens at the internal diameter of the annular ring. The greater the thickness of the lens at the internal diameter of the annular ring, the greater the radial length may be extended before the exterior diameter approaches the predetermined minimum thickness.

If an imaginary line is drawn to connect the second surface's internal diameters of the annular rings, which is the point most distant from the anterior surface, and the center of the central disk, the imaginary line will form an arc or parabola, depending on the various thicknesses chosen. This imaginary line forms the effective second surface 44. By changing the thicknesses and widths of the central disk and annular rings, the effective second surface may be shaped as desired. This is particularly relevant for applications in which the implanted lens is implanted posterior from the iris. This is because the effective second surface may thereby be constructed in a predetermined shape, which enables the implanted lens to be properly near the anterior surface of the natural lens capsule.

As shown in FIG. 24A, in one alternate embodiment of the invention, the central disk 12 and each annular ring 54 of the second optical surface 51 are not planar. Rather, each surface of the central disk 12 and the outer surface 59 of each annular ring 54 is convex. In a second alternate embodiment of the invention, as shown in FIG. 24B, each surface of the central disk 112 and outer surface 159 of each annular ring 154 is concave. Thereby, particular degrees of convexity or concavity of each section of the second optical surface 151 may be chosen to further help obtain particular focusing powers for different lenses. Reference number 59 represents the outer surface of an annular ring 54 of a lens 10 having a convex shape. Reference number 159 represents the outer surface of an annular ring 54 of a lens 10 having a concave shape. Claim language referencing the outer surface could apply to either. Reference number 12 represents the central disk of a lens 10 having a convex shape. Reference number 112 represents the central disk of a lens 10 having a concave shape. Claim language referencing the central disk could apply to either. Also, in any of these embodiments, the central portion and annular rings 54 of the lens 10 may be of a symmetric or asymmetric ovular shape for correction of spherical aberrations.

As best seen in FIGS. 4 and 22–24, the second surface 44 of the lens 10 comprises a central disk 12, which is radially surrounded by a series of annular rings 14, the central disk 12 and the series of annular rings 14 forming a series of radial steps along the second surface 44. Each annular ring 54 has a first section 56, a second section 58, and an outer surface 59, as shown in FIGS. 4 and 22–24. The thickness of the lens 10, or separation between the first section 56 of the annular ring 54 located on the second surface 44 of the lens 10 and the first surface 46, is less than or equal to the predetermined maximum thickness. Also, the thickness of the lens 10, or separation between the second section 58 of the annular ring 54 located on the second surface 44 of the lens 10 and the first surface 46, is greater than or equal to the predetermined minimum thickness. The minimum separation distance from the first surface 46 to the closest point of the second surface 44, the second section 58 of an annular ring 54, is 0.025 millimeters. The maximum separation distance from the first surface 46 to the most distant point of the second surface 44, the first section 56 of an annular ring 54, is 0.45 millimeters. Reference number 46 represents the first surface of a lens 10 having a convex shape. Reference number 146 represents the first surface of a lens 10 having a concave shape. Claim language referencing the first surface could apply to either.

In certain embodiments, the periphery of the optical portion comprises a parallel lenticular area. The parallel lenticular area is of uniform thickness. The parallel lenticular area prevents the phenomenon known as edge effects, which occurs if the optical portion of the lens does not adequately cover the periphery of the pupil. The edge effects are produced in various situations including when overhead lights are illuminated in low lighting situations, such as in roadway tunnels.

Figure 17:
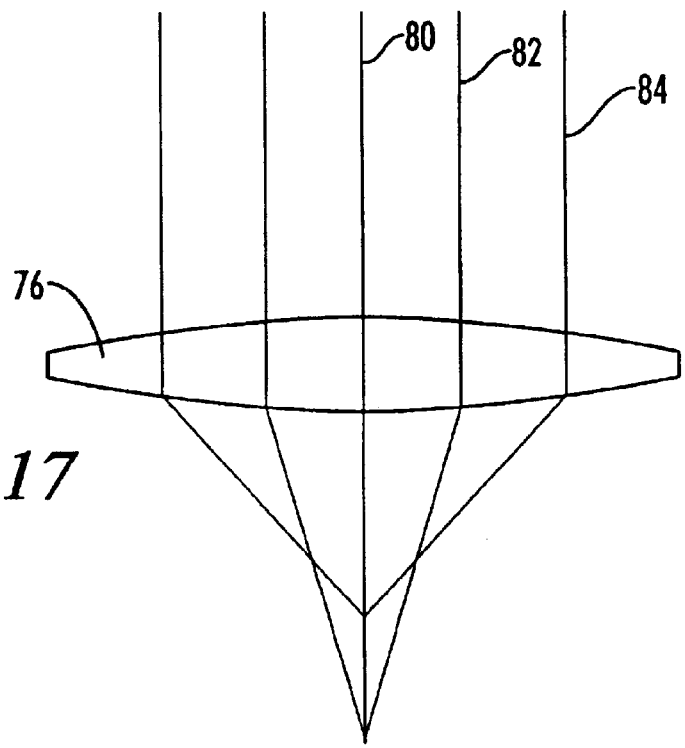
FIG. 17 shows a standard lens 76 with a typical thickness for a given power of 20 diopter when using a material with an index of refraction for 1.47. The figure depicts a ray of light 80 entering the lens at the apex of the lens and passing through the lens without being refracted, which is known as the prime meridian and is along the central axis of the lens. A second ray 82 one millimeter from the prime meridian and parallel to the prime meridian is shown where the refraction is such that the ray comes to a focal point before the prime meridian. The calculations in table 2 show that the focal point of the second ray 82 entering the lens one millimeter from the prime meridian focuses approximately one millimeter before the prime meridian focal point. A third ray 84 entering the standard lens 76 two millimeters from the prime meridian is shown to focus approximately 3 millimeters before the prime meridian.
Figure 18:
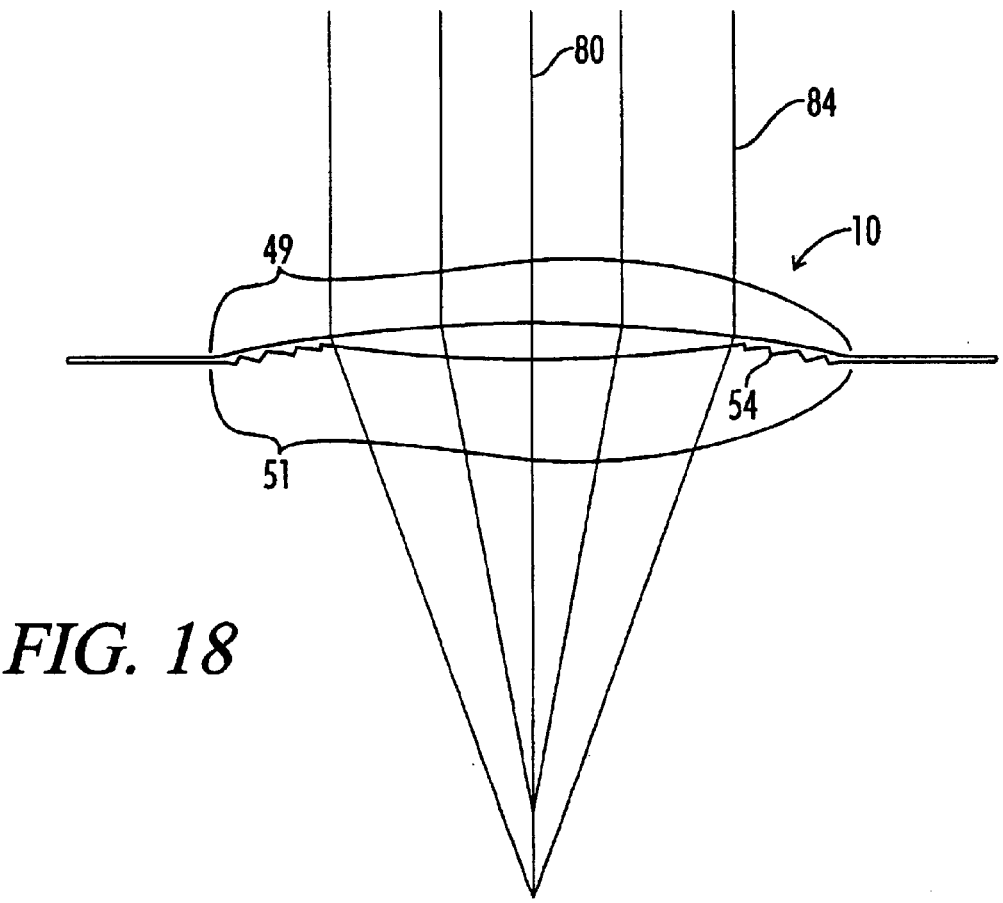
FIG. 18 depicts a ray of light 80 entering the lens at the apex of the lens 10 and passing through the lens without being refracted, which is known as the prime meridian and is along the central axis of the lens. The figure also shows that by adjusting the power on the second optical surface 51 with each ring 54, the focal point of the prime meridian and the third ray 84 entering the lens 10 of the present invention two millimeters from the prime meridian focus at the same point. Therefore, spherical aberrations are reduced.

The first optical surface 49 of the lens 10 is spherical as described in the Gaussan lens theories, yet practical applications have shown the lens design creates spherical aberration as shown in FIG. 18. FIG. 17 shows light rays 80, 82, and 84 entering a standard lens 76. Note that there is more spherical aberration as the distance from the prime meridian of the eye and lens increases. A practical consequence of this condition is the visualization of glare, halos, or rings. Specifically, in low light conditions, such as driving at night, the patient has a much more open pupil. Accordingly, patients often report glare, halos and rings.

With the ultra thin lens 10 disclosed herein, as shown in FIG. 18, much of the spherical aberration present in a standard lens is eliminated. Spherical aberrations cause images to have a ghost or second image. Headlights from on coming vehicles at night will show as a second headlamp or look much larger than actual. The same effect is true of taillights as approaching an automobile. Street lamps can have the same effect. The condition is severe enough in many patients that no attempt is made to drive at night. This is also true of people who wear contact lenses or spectacles.

The following information shows the calculations for spherical aberration for a twenty-diopter lens made from a material with an index of refraction of 1.47.

| | | |
|---|---|---|
| $P =$ | 20 | Total Lens Power |
| $N_{lens} =$ | 1.47 | Index of refraction of the material |
| $N_{aqueous} =$ | 1.336 | Index of refraction of the aqueous of the human eye |
| $R_{total} =$ | $(N_{lens} - N_{aqueous})*1000/P_s$ | Formula assumes one equivalent radius for the lens |
| $R_{total} =$ | 6.7 | Surface radius |
| $Fl_{PM} =$ | $N_{lens}/P_{surface}$ | Focal length of the lens along the prime meridian |
| $=$ | 73.5 | Focal length calculated |
| | Sin    Angle | Angles are in radians |

-continued

| | | | |
|---|---|---|---|
| $Fl_{1\ mm}$ | | | Calculations of the focal length for a ray entering the eye one millimeter from the prime meridian. |
| $\phi_1 =$ | 0.149254 | 0.149814 | Angle 1 formed by parallel light entering the lens and the angle made with the radius of curvature of the lens at the point of contact of the parallel light. In this the calculation one millimeter from the prime meridian |
| $\phi_2 =$ | 0.135648 | 0.136068 | Angle 2 Formed by the light ray as it is refracted and bent in portion to the indexes of refraction of the lens material and aqueous. |
| $\phi_3 =$ | 0.013605 | 0.013746 | Angle 3 Resulting angle between the prime meridian and the refracted light ray. |
| $Fl_{1\ mm} =$ | 72.75212 | 72.74525 | Focal length of the light ray entering the eye at one millimeter from the prime meridian. |
| $D\ Fl_{1\ mm} =$ | 0.747881 | 0.754754 | Difference in the focal length of the prime meridian and the ray that entered the eye one millimeter from the prime meridian. |
| $Fl_{2\ mm} =$ | | | Calculations of the focal length for a ray entering the eye two millimeter from the prime meridian. |
| $\phi_1 =$ | 0.298507 | 0.303128 | Angle 1 formed by parallel light entering the lens and the angle made with the radius of curvature of the lens at the point of contact of the parallel light. In the calculations two millimeters from the prime meridian was selected as the contact point. |
| $\phi_2 =$ | 0.271297 | 0.27474 | Angle 2 Formed by the light ray as it is refracted and bent in portion to the indexes of refraction of the lens material and aqueous. |
| $\phi_3 =$ | | 0.028389 | Angle 3 Resulting angle between the prime meridian and the refracted light ray. |
| $Fl_{2\ mm} =$ | 70.45092 | 70.43199 | Focal length of the light ray entering the eye at two millimeters from the prime meridian. |
| $D\ Fl_{2\ mm} =$ | 3.04908 | 3.068006 | Difference in the focal length of the prime meridian and the ray that entered the eye one millimeter from the prime meridian. |

Figure 19:
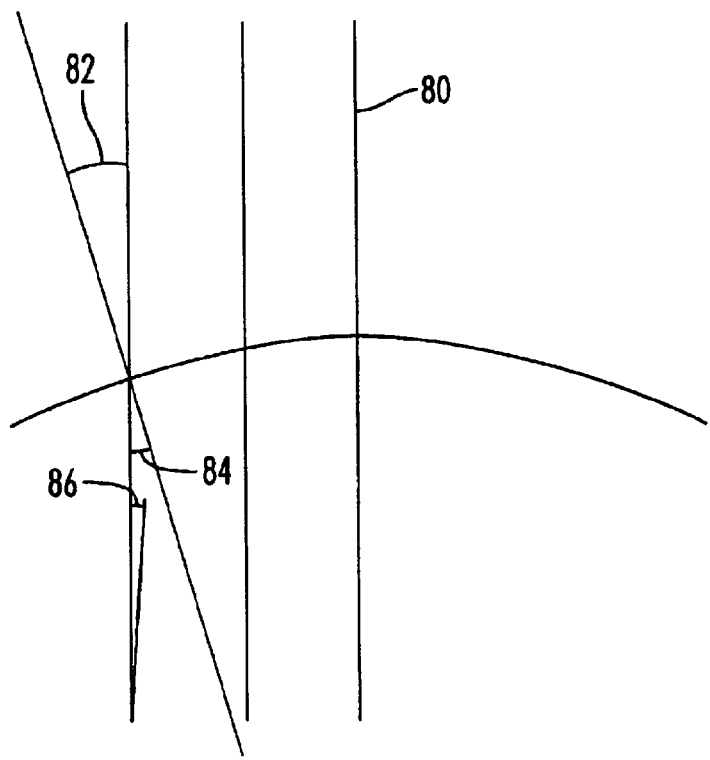
FIG. 19 provides a graphical depiction of the angles described in the calculations for spherical aberration for a twenty-diopter lens made from a material with an index of refraction of 1.47.

The index of refraction of many of the poly hema materials is approximately 1.47. The calculations were based on one lens surface having all the power without showing thickness. This is often done to represent simplified calculations of the lens formula and is approximately accurate to show proof of principle. Therefore, all the power was put into one lens surface and the radius for a 20-power lens is 6.7 millimeters. The radius is determined by dividing the desired power into the difference between the index of refraction of the surrounding media of the lens and the lens index of refraction. The resultant is multiplied by 1000 to convert from meters to millimeters. The focal length of the prime meridian is the resultant of dividing the power into the index of refraction of the material and for the given conditions is 73.5 millimeters. Angle one 82, angle two 84 and angle three 86 described above are depicted in FIG. 19. The angle between the given radius and the ray that contacts the lens at that point is angle one 82. Angle one 82 will vary in value as the distance from the center of the lens the ray being evaluated contacts the lens. Angle two 84 is the angle determined by the formula shown above for determining the amount of refraction. The amount of refraction is a measure of the ratio of the sine of the angles being equal to the ratio of the refractive indexes of the materials. Angle two 84 is the index of refraction of the aqueous divided by the index of refraction of the lens material times the sine of angle one. Note for small angles, the sine of the angle and the angle are approximately equal. The calculations show all angles in radians. Angle three 86 is the angle the refracted ray makes with the prime meridian 80 and is the result of subtracting angle two from angle one. The focal length of the ray entering one millimeter from the prime meridian is obtained by dividing the tangent of angle three into one. The focal length for the ray entering two millimeters from the prime meridian is calculated in a like manner. The difference in the focal length of the prime meridian and the ray entering one millimeter from the prime meridian is approximately 0.75 millimeters short of the prime meridian. The difference in the focal length of the prime meridian and the ray entering two millimeters from the prime meridian is approximately 3 millimeters short of the prime meridian.

The current invention adjusts the radii of curvature on the second surface 44 of the lens 10 to allow the focal point of the rays to be approximately the same as the prime meridian. By doing so, much of the spherical aberration is eliminated.

Figure 20:
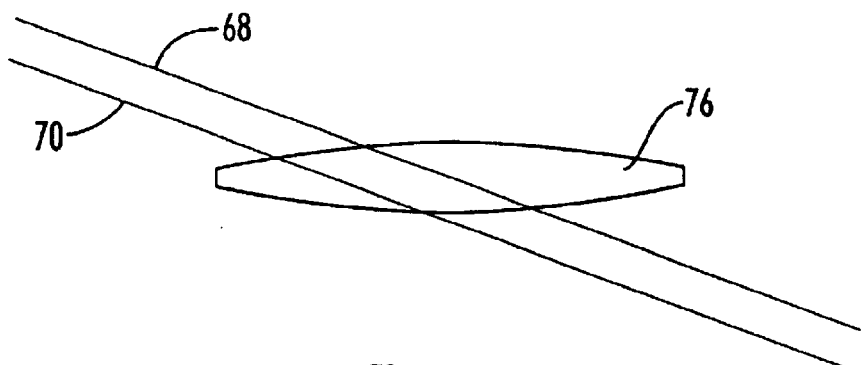
FIG. 20 shows a condition called coma, in which light from ray one 68 travels for over 2.2 millimeters within the standard lens 76 and light from ray two 70 is only passing through the lens for a distance of 1.96 millimeters. Coma appears as a comet or ghost image. The extremely thin lens 10 of the current invention should eliminate much of the coma.

As best seen in FIG. 20, the second of the Third Order Aberrations is coma (Fundamentals of Optics, Jenkins and White, page 162). Coma is described as an off axis spherical aberration, which means that light enters the eye at an angle such that some rays of light travel through the lens longer than other rays. According to the text Clinical Optics, the condition called coma "is spherical aberration applied to light coming from points not lying on the principal axis. Rays passing through the periphery of the lens are deviated more than the central rays and come to a focus nearer the principal axis. This results in uneven magnification of the image formed by different zones of the lens." (A. R. Elkington, H. J. Frank, and M. J. Greaney, Clinical Optics, Third Edition, page 96, Blackwell Science Ltd., Commerce Place 350 Main Street, Malden Mass. 02148 5018, British Library Number ISBN 0-623-04989-8, Library of Congress 99-20296). Authors Jenkins and White state that this condition has the appearance of a commit, therefore the name coma. Coma, like spherical aberrations, causes the patient to see glare halos and rings. Much of the coma is eliminated with the lens 10, described herein, since such a thin lens reduces the travel distance of the light inside the lens 10.

Figure 21:
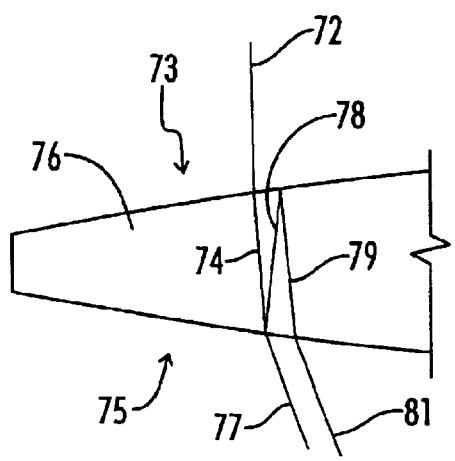
FIG. 21 shows light 72 entering a standard lens 76. The light 72 is refracted by the first surface 73. The refracted light travels toward the second surface 75. Most of the light 72 is refracted by the second surface 75 of the standard lens 76 and the refracted light 77 exits the lens, but a small portion is reflected light 78 which moves toward the first surface 73 of the standard lens 76. Most of the light is refracted again by the first surface 73, but a portion of the reflected light 78 is reflected again such that the reflected light 79 moves to the second surface 75 and again is refracted by the second surface 75 so that the light 81 exits the lens. Several harmonics of the distortion can occur. Each additional image that is projected from the second surface 75 is out of phase with the original refracted ray 77, which will cause distortion.
Figure 22:
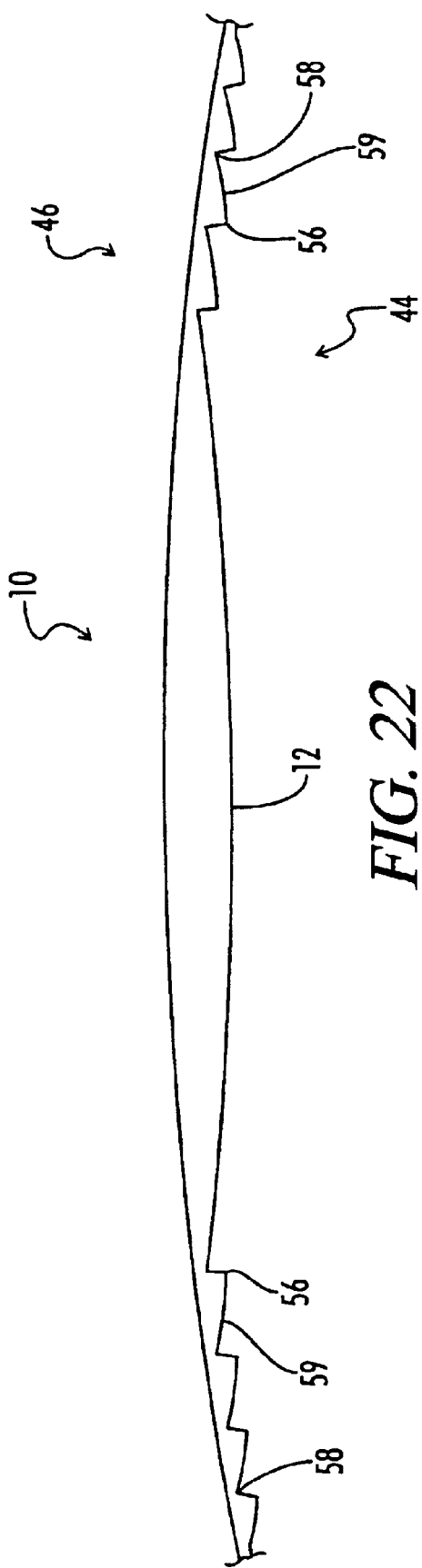
FIG. 22 shows a cross section view of an embodiment of the invention in which the first surface 46 and the surfaces of the central disk 12 and each of the annular rings 54 are convex.

Another of the Third Order Aberrations is distortion. Distortion can come from many sources, one of which is outlined in FIG. 21. As seen in FIG. 21, light 72 is refracted at the first surface 73 of a standard lens 76 and the refracted ray 74 travels through the lens material to the second surface 75 of a standard lens 76. The refracted ray 74, upon contacting the second surface 75 is refracted a second time and the refracted ray 77 exits the standard lens 76. However, some of the light that traveled the same path as the refracted ray 74 is reflected and such reflected light 78 travels toward the first surface 73. Again, a portion of the light is reflected by the first surface 73 of the standard lens 76 and the reflected light 79 returns to the second optical surface where it was initially reflected. Note that the light 81 is out of phase with the refracted ray 77 exiting the lens. Several such harmonics can have an effect on the lens quality. The lens 10, described herein will create less opportunity for the light to be out of phase. While some phase shift is still present, the shift is not as great with the lens 10 of the present invention.

A fourth member of the Seidel sums and Third Order Aberrations is astigmatism of the lens. Most astigmatism was created in older lenses from the polishing process. Most modern intraocular lenses are tumble polished in a process similar to a lapidary. If the cutting process is of excellent quality, then little astigmatism should be present in a modern intraocular lens.

The last of the Seidel sums is curvature of field (Fundamentals of Optics, Jenkins and White, page 170). In previous discussions within this disclosure, we stated that light rays from the outside portion of a standard lens focus earlier than the rays from the center portion of the standard lens. When projecting on a screen, curving the screen can correct the aberrations from curvature of field. The present invention includes correction of curvature of field in the corrections on the second optical surface 51 to correct for spherical aberrations.

All the aberrations focus light at a point other than the point where the prime meridian, located along the central axis of the lens, focuses light. If all the aberrations are present in a lens, then the useful depth of field is reduced. Depth of field is defined as a "range (of distances) in which an image created by an optical system is acceptably sharp" (Dictionary of Eye Terminology, Third Addition, Barbara Cassin and Sheila A. B. Solomon, Triad Publishing Co, Gainesville, Fla., ISBN 0-937404-44-6). By eliminating the aberrations, one can readily conclude the depth of field is greater. With a greater depth of field the patient can see images clearer over a range of distances. Therefore, eliminating the aberrations increases depth of field and gives the patient better ability to clearly see objects near and far without additional corrections.

The following description of Hooke's Law is provided in order to explain why certain materials will bend without distortion before it reaches its elastic limit. According to Hooke's Law when a force is applied along an axis the increase in length due to application of the force divided by the original length of the member along the axis to which the force was applied is strain (Mechanics of Materials, p. 29, E. P. Popov, Professor of Civil Engineering University of California Prentice-Hall, Inc. Englewood Cliffs, N.J. copyrighted 1952 eight printing 1958). Strain is a dimensionless quantity and is very small except for materials such as rubber. Stress is the amount of force applied to a material divided by the cross sectional area of the material where the stress was applied. When plotting a relationship between stress and strain, there is a portion of the diagram that is linear. The deflections where the stress-strain diagram is linear do not cause a permanent deformation of the material to which the stress was applied. For some materials, such as cast iron and concrete, the portion of the curve where there is no permanent deformation is extremely small. For some alloy steels the curve is linear almost to the rupture point of the material. Up to some point the relationship between stress and stain may be said to be linear for all materials. This is known as Hooke's Law.

Stress is directly proportional to strain and the constant of proportionality is called the elastic modulus, modulus of elasticity, or Young's modulus. The elastic modulus has been bench tested and calculated for many materials and published in engineering and other scientific handbooks. In the formula (Standard Handbook for Mechanical Engineers, p.5–42, Theodore Baumeister, Editor Lionel S. Marks, Editor, 1916 to 1951. Mc Graw-Hill Book Company, New York), the amount of deflection is proportional to the applied force times the length of the deflected object to the third power divided by the modulus of elasticity times a coefficient and the moment of inertia of the material being deflected.

Figure 16A:
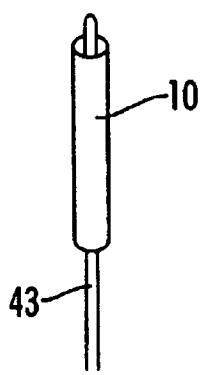
FIG. 16A is an intraocular lens 10 as described by the current invention being rolled around a rod 43. The lens 10 was just removed from a vial containing a balanced salt solution, BSS, which was heated to approximately 100 degrees F. The lens 10 must be rolled immediately after removal from the warm BSS, since the material becomes stiff when cooled or dehydrated.

The formula was used by the authors to calculate the maximum thickness of a lens without exceeding the elastic limit of the material. The value was theoretical since the lens is a wafer or disc and not a true beam. In addition, the modulus used was for an acrylic, which is close to polymethylmethacrylate (PMMA). The theoretical calculations show the maximum thickness of the lens to be 0.25 millimeters. Wafers of PMMA were manufactured by the authors to 0.25 millimeters, which had some permanent deformation when rolled around a ⅛-inch, 3.175-millimeter rod. Test conducted by the authors showed the lens thickness was close to being correct. Next, the authors had lenses with the desired central disk 12 and series of annular rings 14 made; which were rolled by the authors around the ⅛-inch rod. Again, some permanent deformation was present. The experiments were continued until the authors were successful rolling a lens 10 having a maximum thickness of 0.1 millimeters and a minimum thickness of 0.025 millimeters around a ¹⁄₁₆-inch, 1.5875-millimeter rod. A lens 10 with a thickness of 0.1 mm is rolled around a ¹⁄₁₆-inch, 1.5875-millimeter rod 43, as seen in FIG. 16A. Accordingly, in certain embodiments, a lens 10 having a maximum thickness from about 0.1 mm to a minimum thickness of about 0.025 mm is used in the invention described herein. In other embodiments, the lens 10 has a maximum thickness from about 0.45 mm to a minimum thickness of about 0.025 mm. In still other embodiments, the lens 10 has a maximum thickness from about 0.065 mm to a minimum thickness of about 0.025 mm. When the minimum thickness of the lens when measured from the front first surface to the closest minimum point along the second surface is less than 0.025, the lens sometimes fail from shear stress when an instrument to roll the lens is applied. The thin lens formula states $$1/f = (N1-1)(1/R1 - 1/R2)$$

(Fundamentals of Optics, p. 67 and 70, Francis A. Jenkins and Harvey E. White, Fourth Edition, McGraw-Hill Book Company, copyright 1950 and renewed in 1965)

'f=focal length of the lens

N1=index of refraction of the lens material

R1 is one radius of curvature expressed in meters

R2 is the second radius of curvature expressed in meters

The formula is for a lens in air. If the lens is in a media other than air, such as aqueous of the human eye, or other intraocular fluid, the formula becomes $$1/f = (N1-N2)(1/R1 - 1/R2)$$

Where N2 is the index of refraction of the media in which the lens is placed. In this case the aqueous of the human eye.

The power of a lens is P=1/f

Where P is in diopter

'N1 for polymethylmethacrylate is 1.492

'N2 for aqueous is 1.336

Where Tc=the center thickness at the apex=0.1 millimeter

Pa=anterior power

Pp=posterior power

Pn=net power

Below is shown information for a lens where the negative power is expressed net power. First, myopic lenses, followed by hyperopic lenses:

| Pn | Pa | Pp | Center Thickness | Te_2 | Te_3 |
|---|---|---|---|---|---|
| −10 | 5 | −15 | 0.1 | 0.23 | 0.40 |
| −10 | 10 | −20 | 0.1 | 0.23 | 0.41 |
| −10 | 15 | −25 | 0.1 | 0.24 | 0.43 |
| −15 | 5 | −20 | 0.1 | 0.30 | 0.56 |
| −15 | 10 | −25 | 0.1 | 0.30 | 0.58 |
| −15 | 15 | −30 | 0.1 | 0.31 | 0.61 |
| −20 | 5 | −25 | 0.1 | 0.37 | 0.72 |
| −20 | 10 | −30 | 0.1 | 0.37 | 0.76 |
| −20 | 15 | −35 | 0.1 | 0.38 | 0.82 |
| −25 | 5 | −30 | 0.1 | 0.44 | 0.91 |
| −25 | 10 | −35 | 0.1 | 0.45 | 0.97 |
| −25 | 15 | −40 | 0.1 | 0.46 | 1.07 |

| Cataract or Hyperopic Lens | | | | | |
|---|---|---|---|---|---|
| Pn | Pa | Pp | Tedge | Tcenter2 | Tcenter3 |
| 10 | 5 | 5 | 0.2 | 0.33 | 0.49 |
| 10 | 10 | 0 | 0.2 | 0.33 | 0.49 |
| 10 | 5 | 5 | 0.2 | 0.33 | 0.49 |
| 15 | 10 | 5 | 0.2 | 0.39 | 0.64 |
| 20 | 10 | 10 | 0.2 | 0.46 | 0.78 |
| 25 | 10 | 15 | 0.2 | 0.52 | 0.93 |

Te_2 is the distance along the edge of the lens parallel to the central axis and two millimeters from the central axis when the optic diameter is four millimeters. Te_3 is the distance along the edge of the lens parallel to the central axis and three millimeters from the central axis when the optic diameter is six millimeters. The distance from the apex of the anterior surface to the edge of the anterior surface measured parallel and offset to the central axis or prime meridian is expressed as Tr1. The distance from the apex of the posterior surface to the edge of the posterior surface measured parallel and offset to the central axis or prime meridian is expressed, as Tr2. Tc is the center thickness at the apex. The last column shows the edge thickness of the lens. Note the edge thickness, in the best case, approaches the theoretical maximum thickness to where PMMA will roll. From actual experiments, the material does not return completely to the original shape i.e., there is some permanent deformation in the material at 0.25-millimeter thickness. Therefore, the lens will not roll around a ⅛-inch dowel pin and is not a deformable refractive lens. In fact, previously designed lenses do not have a constant thickness along the optic surface where the anterior surface and the posterior surface are parallel to each other. With a thin lens, the radii of each surface approximates each other so that both surfaces have the same power, while the anterior surface is positive and the posterior surface is negative, i.e. the lens powers cancel each other. Note when the lenses are made from a material such as a hydrogel, hydrophilic acrylic or hydrophobic acrylic the lenses flex with much more thickness than PMMA; and the thickness can be increased to approximately one half or less thickness of a standard lens, so the mass is reduced with the current invention, which allows for the smaller incision.

In an article by Doctor Glasser (Glasser and Kaufman, Presbyopia: A View, The eMedicine Journal, Aug. 20, 2001, Volume 2, Number 8, pages 1-15), within the introduction, the author states that presbyopia is characterized as a progressive, age-related loss of accommodative amplitude. Complete loss of accommodation usually culminates by age 50 years. Emmetropic patients have good far vision, but need correction for near vision. Myopic patients near vision is less of a problem.

Figure 15:
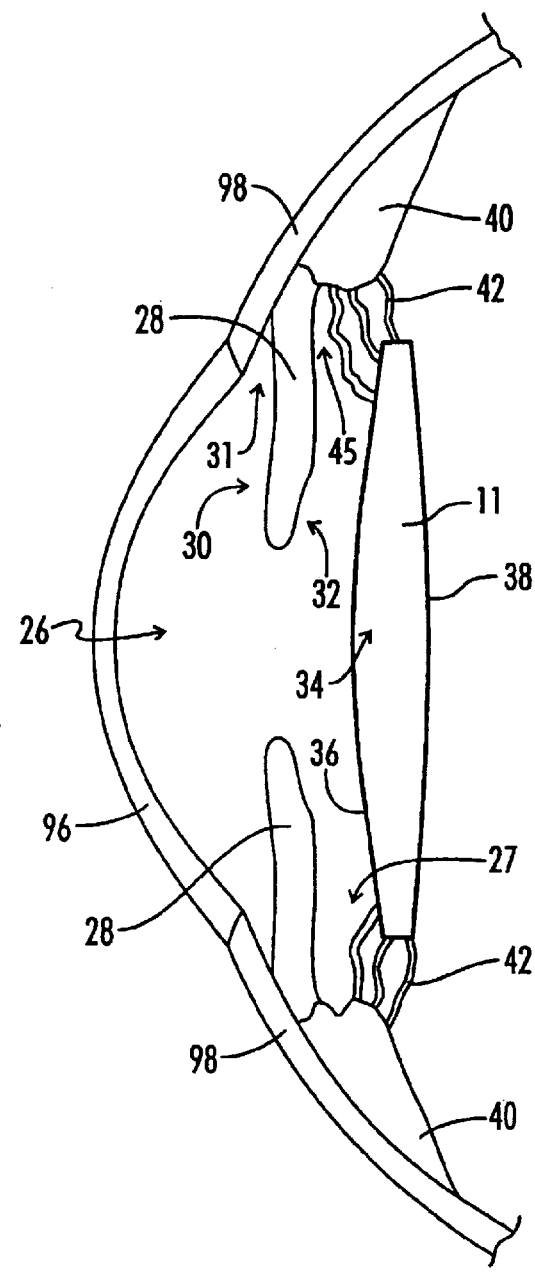
FIG. 15 shows a cross sectional view of an eye. The figure shows the natural crystalline lens 11 of the eye, the anterior chamber of the eye 26, the posterior chamber of the eye 27, the iris 28, the anterior surface of the iris 30, the posterior surface of the iris 32, the anterior surface 36 of the natural lens sac 34, the posterior surface 38 of the natural lens sac 34, the zonules 42, and the ciliary body 40.

In the aforementioned article, Dr. Glasser discusses the theory of accommodation proposed by Helmholtz in 1909. The theory of accommodation theorized that accommodation occurs when the ciliary muscle contracts to release the resting zonular tension on the equatorial edge of the lens. Stated another way, the ciliary body 40, shown in FIG. 15, is smaller when the eye is looking far when compared to the size of the ciliary body during visualization of objects that are near. The general anatomy of the eye is shown in FIG. 15. The smaller ciliary body 40 stretches the zonules 42, which are a form of ligaments. The stretched zonules 42 in turn stretch the capsular sac 34 containing the natural crystalline lens 11, which makes the crystalline lens 11 flatter for far vision. The flatter lens causes the images seen by the eye to focus on distant objects. As the ciliary body 40 swells, the tension on the zonules 42, or ligaments, relaxes and the crystalline lens 11 takes a more natural rounded shape, which allows near objects to focus. Dr. Glasser describes several theories as to why accommodation is reduced with age. Accommodation begins leaving the average person by 35 years of age and the completely gone by age 60 years of age. By age 45 to 50 years of age the average person will need reading spectacles or contact lens for near vision.

In the last paragraph of section two of the introduction, the article by Dr. Glasser goes on to say that experiments show that the ciliary muscle moves anterior-inward, and the equatorial edge of the lens moves away from the sclera during accommodation. (Glasser and Kaufman, Presbyopia: A View, The eMedicine Journal, Aug. 20, 2001, Volume 2, Number 8, pages 1-15). Videos using goniovideography were taken using accommodation, which the zonular fibers or ligaments relaxed during accommodation. The article further states that imaging shows that the posterior zonular fibers, extending between the posterior attachment of the ciliary muscle and the ciliary processes, are stretched during accommodation by the forward and axial movement of the apex of the ciliary muscle.

In Section three, entitled Theories of Presbyopia, Dr. Glasser discusses several theories, which state why accommodation is lost. (Glasser and Kaufman, Presbyopia: A View, The eMedicine Journal, Aug. 20, 2001, Volume 2, Number 8, pages 1-15). One of the two predominate such theories is that the crystalline structure of the natural lens becomes brittle with age. Another theory is the loss of ciliary muscle and choroidal elasticity. A similar theory is that the natural lens of the eye continues to grow with age until the muscles cannot over come the force exerted by the lens to allow a change of shape.

If a surgeon removes a cataract early, then the crystalline lens is easy to chop into small segments and aspirate. If the cataract is allowed to mature, then the surgeon will spend an exceptional amount of time in the extraction of the crystalline lens. A cataract with age will become exceeding hard. MRI measurements have shown that the accommodative ciliary ring diameter constriction is reduced in elderly eyes as compared to the younger eyes presented (Strenk, et al., Age-related changes in human ciliary muscle and lens: a magnetic resonance imaging study. Invest Ophthalmology Vis. Sci. May 1999; 40(6): 1162–1169; Also discussed in Glasser and Kaufman, Presbyopia: A View, The eMedicine Journal, Aug. 20, 2001, Volume 2, Number 8, pages 1–15). Elderly ciliary muscles do not allow for as much accommodation. Dr. Glasser went on to summarize work by Tamm (Tamm E, Croft M A, Jungkunz W, et al: Age-related loss of ciliary muscle mobility in the rhesus monkey. Role of the choroid. Arch Ophthalmology June 1992; 110(6): 871–6; Tamm E, Lutjen-Drecoll E, Jungkunz W, et al: Posterior attachment of ciliary muscle in young, accommodating old, presbyopic monkeys. Invest Ophthalmology Vis Sci April 1991: 32(5): 1678–92; Tamm S, Tamm E, Rohen J W: Age-related changes of the human ciliary muscle. A quantitative morphometric study. Mech Ageing Dev February 1992 62(2): 209–21) identifying several aspects that change with age. The total area of the ciliary muscle decreases. Its length decreases almost by one half in adults aged 30–85 years, the areas of the longitudinal and reticular portions of the muscle decrease, the area of the circular portion increases, the connective tissue in the muscle's longitudinal portion increases, and the distance from the muscle's inner apex to the scleral spur decreases.

From Glasser's summary of Helmholtz we learned contraction of the ciliary muscle releases the resting zonular tension on the equatorial edge of the lens; therefore, the ciliary diameter is less and the tension on the zonules is removed. Previously, from Glasser's discussions in section three, under Mechanism of accommodation, we learned the ciliary body moves anteriorly, toward the iris, and the equatorial edge of the lens moves away from the sclera during accommodation. The zonular fibers become relaxed during accommodation. Dr. Glasser goes on to say the ciliary muscle, and ciliary processes are stretched during accommodation by the forward and axial movement of the apex of the ciliary muscle.

Figure 13A:
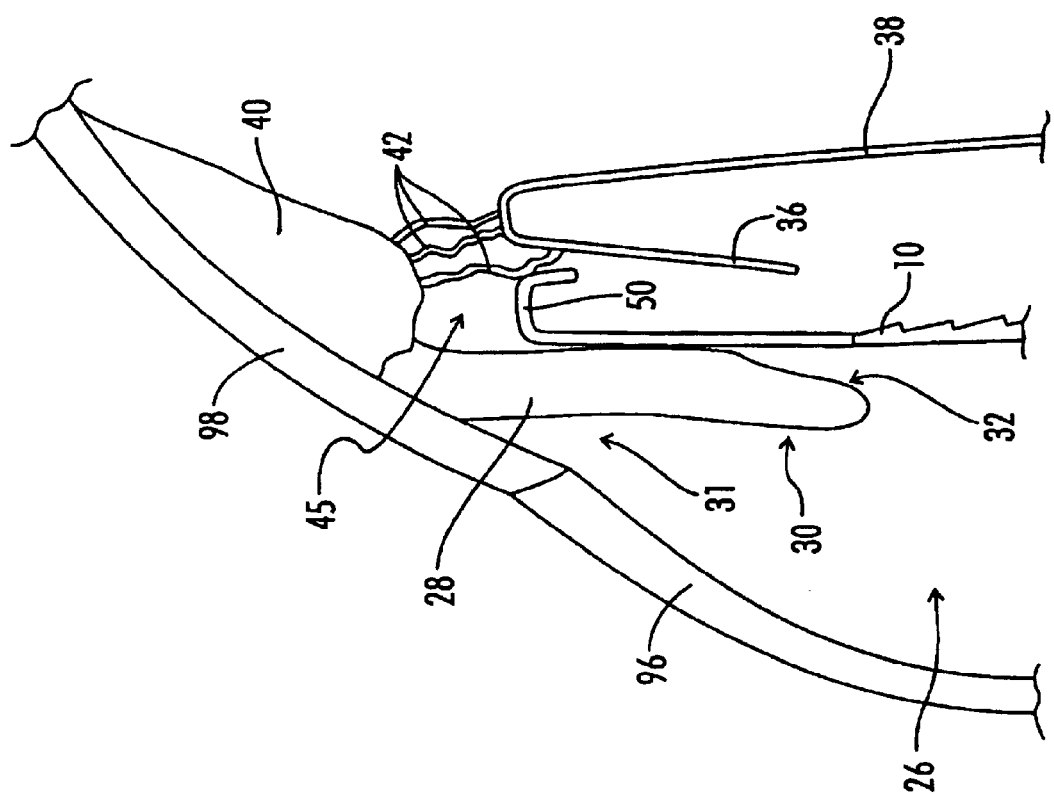
FIG. 13A shows the detail of the anchoring portion 50 of the lens 10 biasing against the zonules 42 and the posterior surface 32 of the iris 28. The anchoring portion 50 is rolling toward the anterior portion of the eye.
Figure 13B:
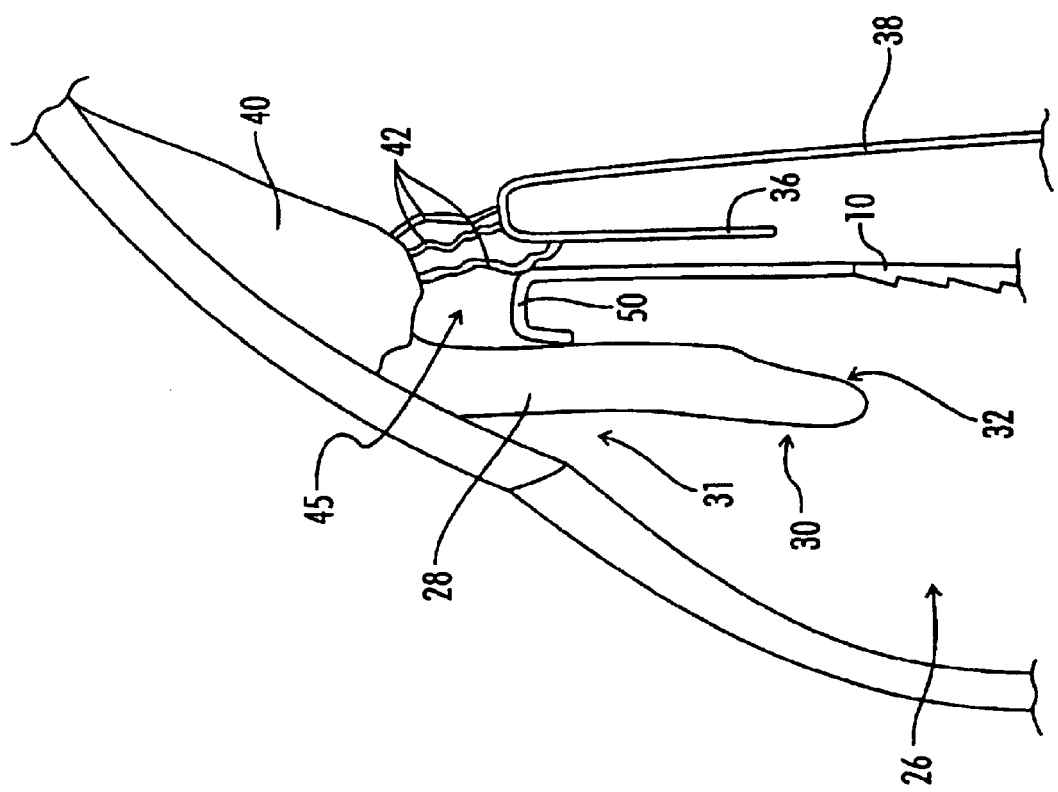
FIG. 13B shows the detail of the anchoring portion 50 of the lens 10 biasing against the zonules 42 and the posterior surface 32 of the iris 28. The anchoring portion 50 is rolling toward the posterior area of the eye.

When intraocular lenses are implanted, the known intraocular lenses produce a force on the haptics and many are vaulted or angled toward the rear of the eye. Even three-piece whisker looking haptics exert force against the equatorial area of the capsular sac. The current invention is an intraocular lens with little or no force exerted by the anchoring portion. In certain embodiments, the lens 10 is positioned to bias against the zonules 42 and the posterior surface 32 of the iris 28, as best seen in FIGS. 13A and 13B. In FIG. 13A, the anchoring portion 50 is rolled toward the anterior portion of the eye. In FIG. 13B, the anchoring portion 50 is rolled toward the posterior area of the eye. In addition to the anchoring portion 50 rolling in different directions, as previously mentioned, the lens 10 may be inserted either with the first surface 46 of the lens 10 facing the anterior chamber 26 of the eye, or the second surface 44 of the lens 10 facing the anterior chamber 26 of the eye.

Figure 10:
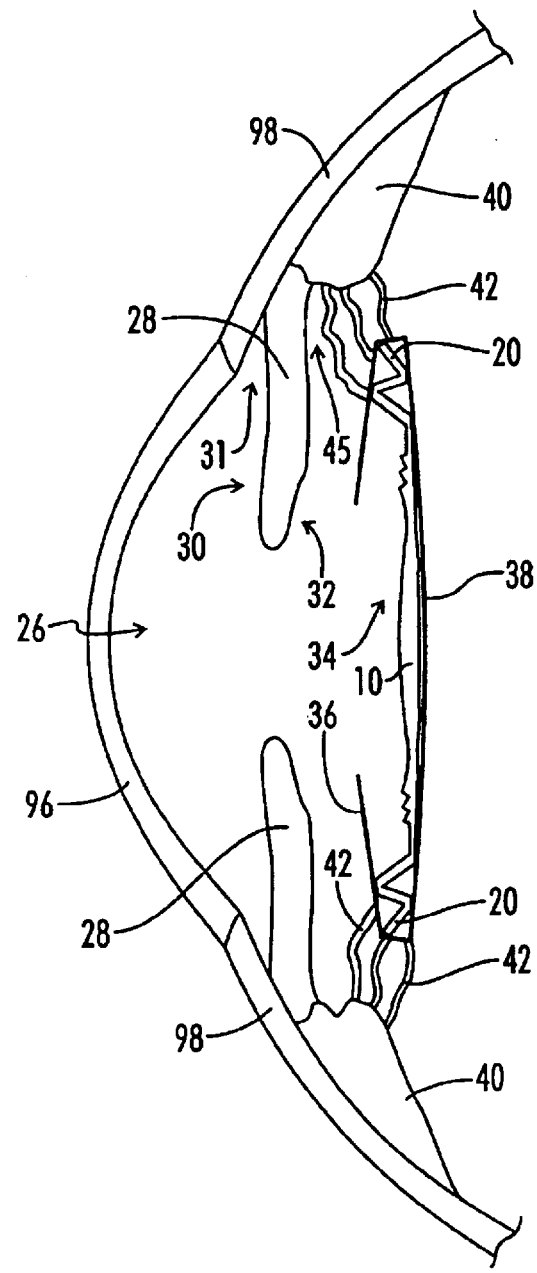
FIG. 10 shows a lens 10 in an aphakic eye wherein the thinner section of the haptic 20 accordions in the sac.
Figure 11:
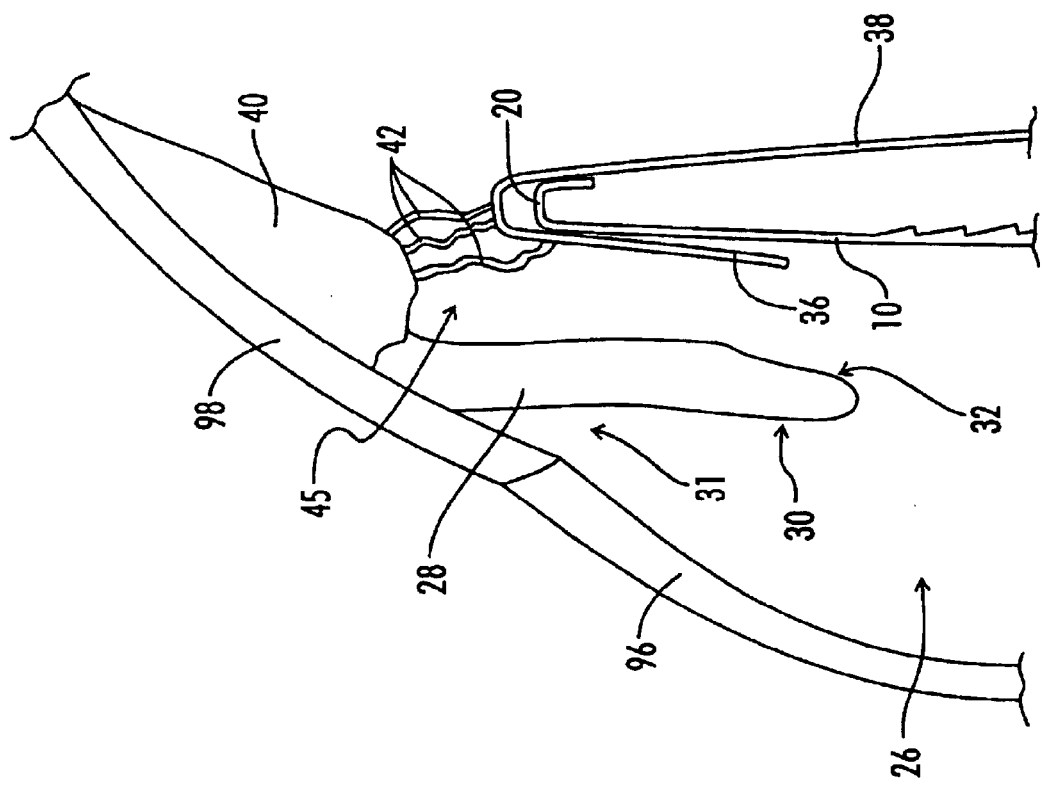
FIG. 11 shows the detail of the anchoring footplate 20 rolling toward the anterior portion of the eye. Note that the anchoring footplate 20, in this embodiment serving as the anchoring portion, is biased against the anterior surface 36 of the capsule 34 and the posterior surface 38 of the capsule 34.
Figure 12:
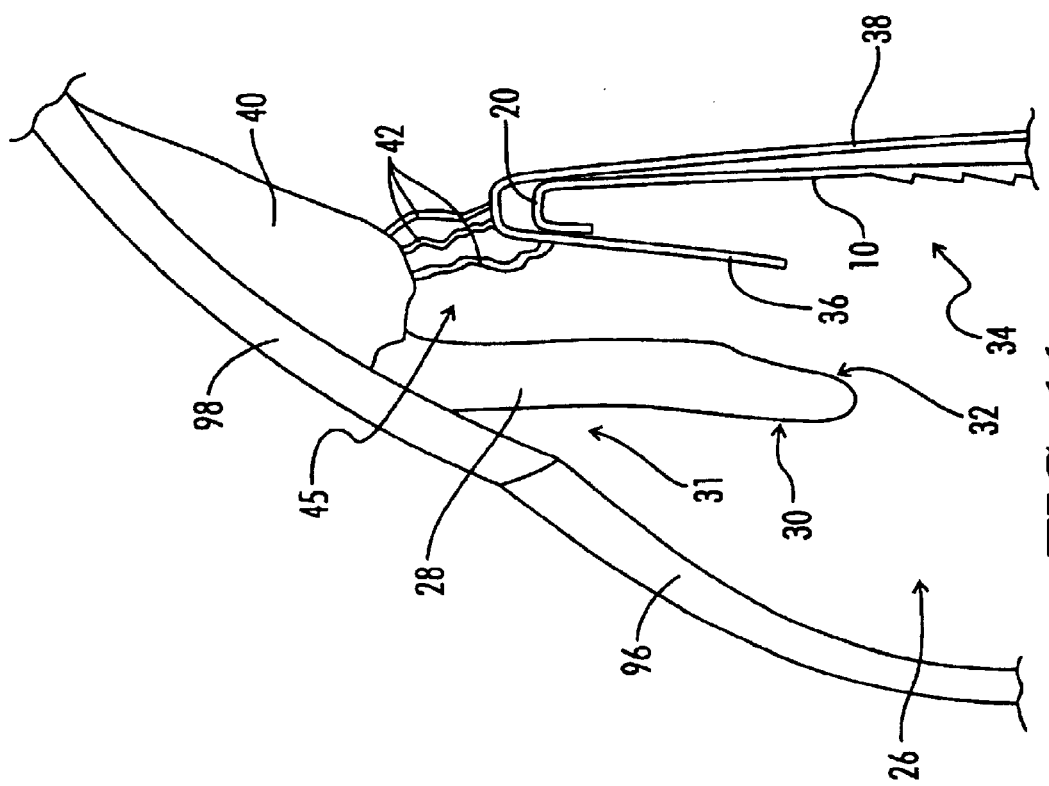
FIG. 12 shows the detail of the anchoring footplate 20 rolling toward the posterior portion of the eye. Note that the anchoring footplate 20, in this embodiment serving as the anchoring portion, is biased against the anterior surface 36 of the capsule 34 and the posterior surface 38 of the capsule 34

In other embodiments, the lens 10 is positioned to bias against the anterior surface 36 of the capsule 34 and the posterior surface 38 of the capsule 34, as seen in FIGS. 10, 11 and 12. In such embodiment, the intraocular lens 10 is placed in the capsule 34 with side forces from the posterior surface 38 and anterior surface 36 of the capsule 34 pinching the haptics footplates 20, serving as the anchoring portion, to hold the less 10 in place. In addition to the anchoring portion 50, represented in the above-mentioned figures by the anchoring footplate 20, rolling in different directions, as previously mentioned, the lens 10 may be inserted either with the first surface 46 of the lens 10 facing the anterior chamber 26 of the eye, or the second surface 44 of the lens 10 facing the anterior chamber 26 of the eye.

Figure 14:
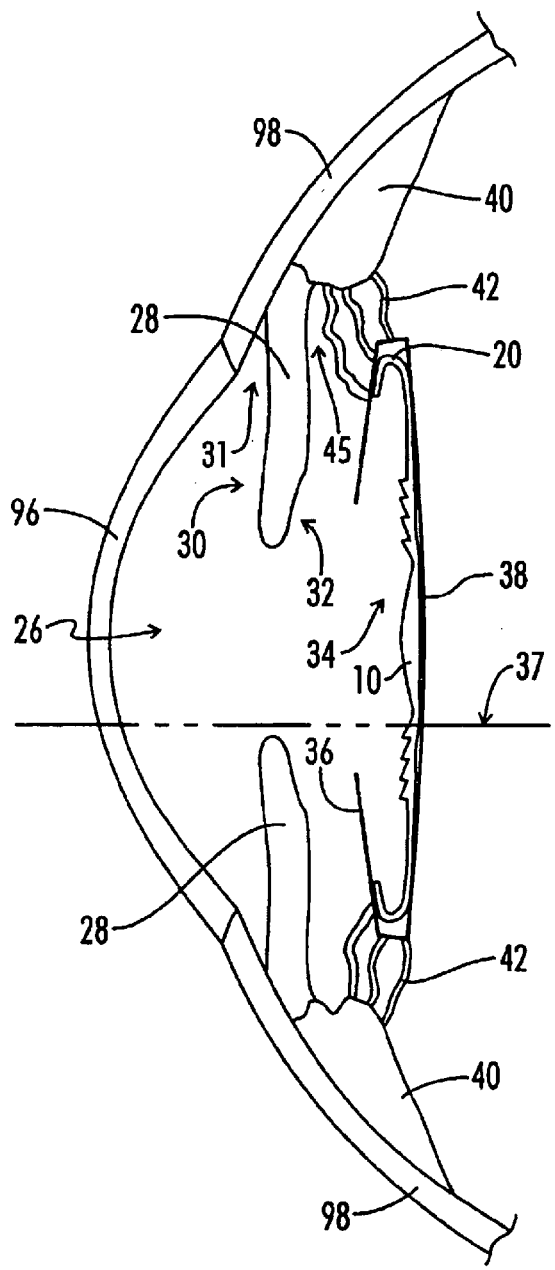
FIG. 14 shows the axis of motion 37 of the lens 10 relative to the eye.

With the eye focused on far objects the ciliary body 40 is relaxed and the zonules are tight, so the lens rest along the equator of the capsular sac. As the eye looks at close objects the ciliary body 40 swells, relaxing the zonules. The ciliary body 40 swelling displaces the vitreous body, which exerts a small force on the posterior capsule and zonules forcing them forward. Since the lens 10 has little or no force exerted to keep the equatorial area of the capsular sac 34 stretched, the zonules 42 are free to move forward. As shown in FIG. 14, the forward movement, depicted by the axis of motion 37, of the zonules 42 cause the capsular sac 34 containing the lens to move forward, which in turn moves the intraocular lens forward, which creates the accommodation.

The invention disclosed herein provides surprising results with respect to correcting the problem of glare, halos, and rings of light. The invention also provides surprising results regarding the correction of a lack of accommodation.

In certain embodiments, the haptic 18 areas can be sloped in the posterior direction, which causes the lens 10 to be positioned behind the equator of the capsular sac 34 or in the direction of the retina. The anchoring portion 50 is also called a haptic 18, anchoring footplate 20, plate haptic 22, or other similar structure. In other embodiments, the haptic 18 areas can also be sloped in the anterior direction, which causes the lens 10 to be position in front of the equator of the capsular sac 34 or toward the iris 28. The haptic 18 areas can also be flat which leaves the lens 10 positioned along the equator of the capsular sac 34. The haptic 18 area being of such a thickness to allow rolling, squeezing or other means of compressing of the optical portion 48 and haptic 18 portion of the lens 10 for insertion into an incision. In certain embodiments, an incision is smaller than 1.5 mm. In other embodiments, the incision is smaller than 2.5 mm. In other embodiments, the incision is about 1.5 mm. In certain embodiments, the optical portion 48 of the lens 10 is constructed of a material different from the material used to construct the anchoring means 50, haptic 18, or anchoring footplate 20. In such an embodiment, the materials may be fused, connected, or attached as commonly known within the art.

In certain embodiments, the anchoring portion 50 of the lens 10 is a plate haptic 22, as shown in FIG. 5. In other embodiments, the anchoring portion of the lens 10 is a plate haptic 22 with markers 24 which indicate the direction or orientation of the lens 10, as shown in FIG. 7.

The number of anchoring footplates 20, also called haptic footplates, can vary from none to eight. In certain embodiments having no anchoring footplates 20, the lens 10 forms a dome design. In other embodiments, as best seen in FIG. 5, the lens 10 can have a plate haptic 22.

As a means for comparison, the optic edge of a standard negative 20-power lens has an edge thickness 0.360 millimeters when the optic diameter is 4 millimeters. For the same power and optic diameter the current invention has an edge thickness of 0.05 millimeters. Note that for the invention by Federov, et al., U.S. Pat. No. 5,258,025, to obtain a 20-diopter negative power lens with a 0.1 millimeter center thickness, the edge of the lens must be 0.348 millimeters. The edge thickness of the current invention with the same optical diameter, 4 millimeters, is 0.0323 mm. However, the current invention has a maximum thickness for a 20-diopter negative power lens of 0.0776 millimeters. As a consequence of the thickness of the lens by Federov, et al., it is too thick to roll since it will exceed the elastic limit of PMMA. Even if the lens by Federov, et al, were made from a material such as a hydrogel or hydrophilic acrylic, the lens would roll or squeeze, but the needed incision size will be significantly larger than the incision size for the current invention.

U.S. Pat. No. 5,076,684, by Simpson, et al., describes a multi-focal lens where there is no attempt to move the anterior and posterior surfaces close together in order to obtain a minimum thickness. Simpson, et al. describe annular rings, but not for the purpose of making the lens thinner. Simpson, et al. state in claim one that at least a portion of said optical power being produced by diffraction. In the 1800's Fresnel developed a diffractive lens having annular rings for use in lighthouses. The use of annular rings to develop multi-focal lens seems to be the bases of the Simpson, et al. patent.

The current invention uses annular rings to create an extremely thin lens 10. In certain embodiments, the function of the annular rings 54 is to allow the lens 10 to be folded or rolled in order to fit through a small incision. In other embodiments, the function of the annular rings 54 is optical in nature as the presence of the annular rings 54 results in the reduction or elimination of glare, halos, and rings of light. The purpose of the intraocular lens 10 is to allow the material to be thin enough to roll without exceeding the elastic limit of the material and to reduce the incision size. None of the aforementioned prior art discusses using annular rings to obtain a lens thin enough to roll without exceeding the elastic limit of the material. In fact, none of the work referenced discusses making a lens thin enough to roll without exceeding the elastic limit of the material, nor do they discuss making such a thin lens to reduce the incision size.

Thin lenses are desirable in order to remove the problem of glare and the visualization of halos and rings of light. Since the first intraocular lenses implantation patients complained of glare, halos and rings from intraocular lenses, it is considered a significant problem. Light catches on the edge and is reflected into the eye. The light is unfocused, but the thick edge reflects light that appears to the patient as a ring or halo. The condition is more noticeable at night when the patient is in dimly lit places with high overhead lighting, such as streetlights or tunnels. The condition exists to some extent even in the middle of the day under bright sunlight. For the current invention described herein, the thin edge 16 of the optical portion 48 is from about 50 microns to about 200 microns thick. That is a very narrow thickness when compared to the standard six-millimeter optic lens, which has an optical portion edge of over 1000 microns for myopic lenses.

The present invention discloses a lens, and method of use thereof, that is used to correct a lack of accommodation. By making the lens thin, and removing material that is present in a thicker lens, the current invention allows for the anchoring means 50, such as an anchoring footplate 20, or a plate haptic 22, to hold the lens in place and be flexible enough to allow axial movement of the lens 10. This axial movement, as shown in FIG. 14, provides accommodation for the patient. Previous designs, such as U.S. Pat. No. 6,197,059, by Cumming, used a hinge concept to allow for movement of the lens. In the current invention the thin design allows the optical portion 48 of the lens 10 to be light enough and the anchoring means 50, such as an anchoring footplate 20, or a plate haptic 22, to be flexible enough for the lens 10 to move with the natural movement of the capsule. Natural movement can come from the removal of tension on the zonules, which allow them to axially move forward, creating natural forward motion.

Figure 16B:
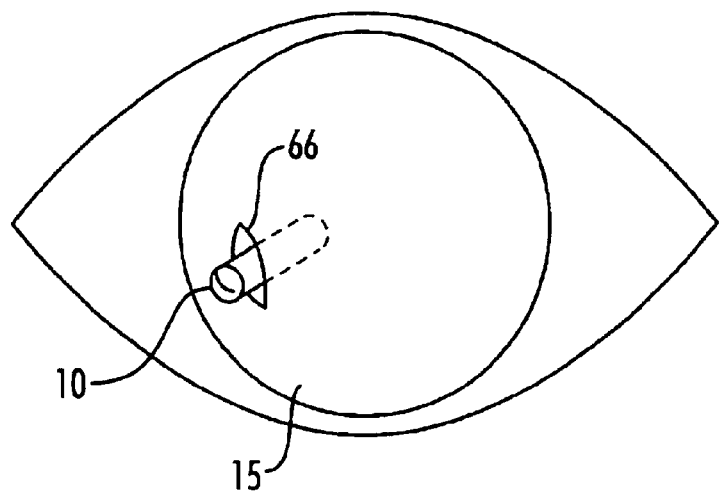
FIG. 16B shows the lens 10 which has slightly penetrated the incision, also called the wound 66, which is smaller than 1.5 mm in length, of the eye 15.
Figure 16C:
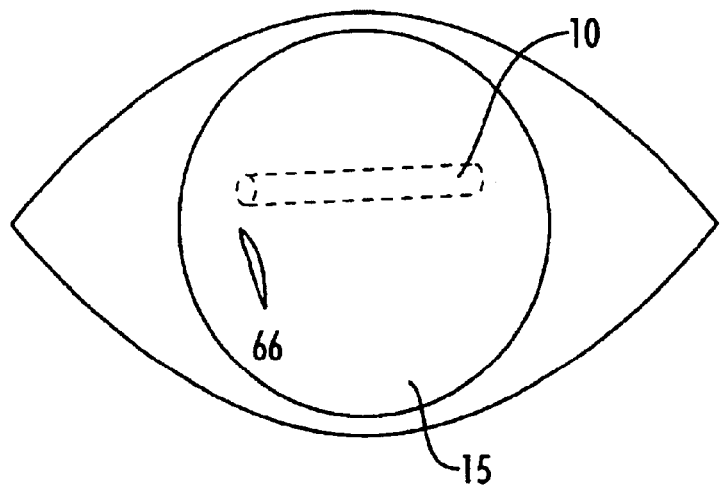
FIG. 16C shows the lens 10 inside the eye 15. Once inside the eye 15, the lens 10 will come in contact with the warm aqueous, or intraocular fluid, of the human eye 15 and immediate begin unrolling, which takes approximately 15 seconds.

As shown in FIGS. 16A, 16B, and 16C, prior to implantation, the lens 10 is rolled to allow for insertion in the incision. The lens 10 may be rolled around an object, such as a rod 43, as shown in FIG. 16A. In other embodiments, the lens 10 may be merely rolled upon itself.

The lens 10 is warmed, or heated, prior to rolling or deforming. In certain embodiments, the lens 10 is warmed to around 100 degrees F. In other embodiments, the lens 10 is warmed to a temperature from about 90 degrees F. to about 150 degrees F. When the lens is cooled to about room temperature, or dehydrates, the lens becomes brittle. In certain embodiments, the temperature of the lens 10 reduced prior to inserting the lens 10 into an incision of the eye. When the lens 10 is re-hydrated, or warmed, as it will be by the fluid present in the eye, the lens 10 will unroll by itself.

In certain embodiments, an incision is cut in the eye so that the lens 10 may be placed therein. Common protocols are well known in the art regarding the instruments for cutting and the location of such incision. In certain embodiments, the incision is less than 1.5 millimeters. In other embodiments, the incision is less than 2.5 millimeters. As shown in FIG. 16B, the lens is inserted through the incision into the eye 15. FIG. 16C shows the lens 10 inserted into the eye 15 and starting to unroll, or deform.

As shown in FIG. 11, in certain embodiments, the lens 10 may be placed in the capsule 34, being biased against the anterior surface 36 of the capsule 34 and the posterior surface 38 of the capsule 34. Also, as shown in FIG. 11, the anchoring portion of the lens may curl toward the anterior direction of the eye. As shown in FIG. 12, the anchoring portion may curl toward the posterior direction of the eye. In other embodiments, the direction of the lens 10 may be reversed. Also, lenses having other concavities and convexities of the first optical surface and the second optical surface may be used as shown in the above-mentioned figures.

In another embodiment, as shown in FIGS. 13A and 13B, the anchoring portion 50 is biased against the zonules 42 and the posterior surface 32 of the iris 28. As mentioned above, the anchoring portion 50 of the lens 10 may curl in the anterior direction, as in FIG. 13A, or in the posterior direction, as in FIG. 13B. In other embodiments, the direction of the lens 10 may be reversed so that the posterior facing surface, as shown in either FIG. 13A or 13B is anterior facing. Also, lenses having other concavities and convexities of the first optical surface and the second optical surface may be used as shown in the above-mentioned figures. Also, the anchoring portion may accordion. Accordion of the anchoring portion 50, in this embodiment an anchoring footplate 20, is depicted in FIG. 10.

In certain embodiments, subsequent to insertion, as the lens 10 unrolls inside the natural lens sac 34 and the lens 10 opens until the anchoring footplates 20, also called haptic footplates, strike tissue. When the anchoring footplates 20 strike tissue, then the lens stops unfolding. The ultra-thin haptic 18 and anchoring footplate 20 exert very little force on the inside of the natural lens sac 34 that originally held the natural lens of the eye. Subsequent to insertion and unrolling of the lens 10, the incision will most likely require no repair, which is well known in the art.

The lens 10 is capable of moving within the natural lens sac 34. When the anterior portion of the ciliary body 40 swells the force on the anterior zonules is reduced. The pressure in the eye then forces the lens 10 forward allowing axial movement. The thin optical portion 48 and thin haptic 18 allow the lens 10 to move axially providing accommodation. In other embodiments, the method of correction a loss of accommodation further comprises curling the haptic footplate 20 toward an anterior surface 36 of the natural lens sac 34, as shown in FIG. 11. In other embodiments, the method of correction a loss of accommodation further comprises curling the haptic footplate 20 toward a posterior surface 38 of the natural lens sac 34, as shown in FIG. 12. In other embodiments, the lens 10 is inserted in a ciliary body 40 of an aphakic eye. In still other embodiments, the lens 10 is inserted and attaches to the posterior surface of the iris 32. When the ciliary muscles relax the lens does not stretch the sack and moves forward. In certain embodiments, the lens 10 is capable of moving within the anterior chamber 26 of the eye. This action creates accommodation for the patient.

The artificial lens is typically manufactured from an acrylic plastic, which can be polymethylmethacrylate (PMMA), or a hydrophobic acrylic with a lower modulus of elasticity allowing the material to roll or bend without permanent deformation. Another acceptable acrylic material is a hydrophilic material, such as a copolymer of hydroxy ethyl ester of methacrylate acid and methyl methacrylate, hydrogel, which has a very high modulus of elasticity and is brittle and glassy when dry but becomes soft and plastic on swelling with water (Plastics Technology Handbook, Third Edition, Manas Chanda and Salil K. Roy, Marcel Dekker, Inc., New York, page 584). Such material is a preferred material because it is biologically compatible with the tissue of the eye, and it does not degrade over time.

The material of manufacture of the lens can be any biocompatible, optically suitable, flexible, and machinable or moldable material with an index of refraction between 1.4 and 2.0. Examples of materials that may be used to manufacture the lens include, but are not limited to, acrylic, hydrophilic acrylic, hydrophobic acrylic, or polymethylmethacrylate (PMMA), Hydrophilic materials with water contents from over 75 percent to 18 percent water used for the manufacture of the current invention can be purchased from Contamac Ltd, Bearwalden Business Park, Saffron Walden Essex, CB11 4JX, United Kingdom. One material is a Poly hydroxy ethyl methacrylate with water content of 38%. A second material is a copolymer of N-vinyl pyrrolidone and 2-hedroxyehtyel methacrylate. Similar materials have water contents as high as 76%. Forms of contact lens materials using a copolymer of alkyl methacrylate with siloxanyl methacrylates and fluorine containing comonomer as also available from the same supplier. For intraocular lenses Contamac produces copolymer of hydroxy ethyl methacrylate and methyl methacrylate with a UV blocker. The water content can vary from 18.5% to 26%. The same company also manufactures PMMA buttons. Other suppliers also manufacture silicone compounds for the molding of lenses.

In certain embodiments, the optical portion 48 is constructed of acrylic, hydrophilic acrylic, hydrophobic acrylic, or hydrogel. In other embodiments, the optical portion is constructed of acrylic and the anchoring portion is constructed of polymethylmethacrylate. In still other embodiments, the optical portion is constructed of hydrogel and the anchoring portion is constructed of polymethylmethacrylate. In other embodiments, the optical portion is constructed of hydrogel and the anchoring portion is constructed of acrylic.

Experience from cataract surgeries shows that the astigmatism will be reduced if a smaller incision is made. It follows that if the lens could be manipulated through a smaller incision, it will reduce the severity of the astigmatism. The optical portion of the intraocular lens, though, must have a diameter of at least approximately 6 mm in order to properly cover the pupil. So, the only way to pass a lens through a smaller incision is to first fold the lens into a U-shape or roll it so that the opposite edges are overlapping. However, currently designed hydrophobic or hydrophilic lenses are either rigid and too brittle to be rolled or folded or when folded still require an incision size of approximately three millimeters, which still produces astigmatism. While it is known that a material which is rigid at a given thickness may be flexible at a lesser thickness, the maximum material thickness under which PMMA is flexible is approximately 0.25 mm. Other acrylic materials have much better flexibility but still require an incision size large enough to create astigmatism.

A lens has a convex first surface into which incident light passes. The lens also has a second surface 44, opposite the first surface, from which the refracted light exits. The second surface 44 may be convex, planar or concave. The power of the lens is determined by the curvature of the first surface 46 and second surface 44.

As shown in FIG. 2, to prevent glare, halos, and rings of light seen by the patient the edge 16 of the optical portion 48 of the lens 10 is extremely thin. In the preferred embodiment the lens edge 16 is 200 microns. To prevent flexing of the optical portion 48, the haptics 18 are thinner than the edge 16. In certain embodiments, the haptic footplate 20 thickness is approximately 50 microns. In other embodiments, the haptic footplate 20 thickness is less than 50 microns. In still other embodiments, the haptic footplate 20 thickness is from about 50 microns to about 200 microns. As described herein, the anchoring portion 50 may be a haptic footplate 20, plate haptic 22, or other type of haptic. The anchoring portion 50 has a thickness of about 10 microns to about 100 microns. In other embodiments, the anchoring portion 50 has a thickness of less than 100 microns. The haptics 18 can have multiple haptic footplates 20 from two to eight. The preferred embodiment has four haptic footplates 20 as shown in FIG. 7. In the preferred embodiment the haptic footplates 20 roll toward the anterior chamber 26 of the eye, as shown in FIG. 11.

Once a surgeon centers the lens 10 in the eye, then the haptic force will hold the lens centered. The thin construction of the haptic 18 places virtually no radially inward pressure on the internal surfaces of the eye.

The exact diameter of a lens 10 is determined by several factors. When a lens 10 is inserted in the natural lens sac 34, also known as the capsular sac, in the posterior location, the lens 10 diameter is such that it fits in the capsular sac 34 where the natural lens has been removed. Alternatively, the lens 10 can be placed in the ciliary cavity 45, located between the posterior surface of the iris 32 and the zonular structure 42, also known as ligaments, of the eye. When the lens 10 is placed in the capsular sac 34, the lens 10 diameter will be from about 10 millimeters to about 14 millimeters with the preferred embodiment to be approximately 11 millimeters. As shown in FIG. 1, the lens 10 diameter is from about 10 mm to about 14 mm. The plate style lens has an angle 94, shown in FIGS. 6 and 8, that can vary from +10° to 0° with the preferred embodiment posterior chamber lens of zero degrees.

In one embodiment, the lens 10 is implanted into the human eye through a 1.5 millimeter incision in the cornea 96 or sclera 98. The steps of rolling the lens 10, inserting the lens 10 in the eye 15, and the initial unrolling of the lens 10 are shown in FIG. 16. Such embodiment uses the ultra thin haptic 18 with the optical portion 48, as shown in either FIG. 2 or 3. During the implantation of this specific embodiment, or any of the other embodiments previously mentioned that describe implantation, the eye is irrigated with a Balanced Salt Solution, BSS, manufactured by one of several pharmaceutical suppliers and labeled as such which are well know to persons with know in the art. In certain embodiments, implantation occurs at around room temperature and the lens unrolls when the intraocular fluid elevates its temperature to a range of about 85° F. to 100° F., with the preferred temperature to be 98.6° F. FIG. 16 depicts the steps of rolling the lens, inserting the rolled lens through the incision, and the initial unrolling of the lens in the eye.

There are many techniques used to enter the eye in order to remove the cataract. The size and location of the incision can affect the curvature of the cornea 96 and potentially induce astigmatism. Having a smaller incision can minimize this. Incisions in the sclera 98 (the white part of the eye) are typically 6 mm in length, whereas incisions in the clear part of the cornea 96 can be considerably smaller (around 3 mm). These corneal incisions are so small, that they usually do not even require sutures to close the wound. Furthermore, unlike cutting in the sclera 98, there is no bleeding associated with making an incision in the cornea 96. The present invention reduces the corneal incision to as small as 1.5 millimeters or less. Many surgeons do what is called bi-manual techniques by inserting two incisions of 1.5 millimeters and removing the cataract through one incision with a phaco emulsification machine. The phaco emulsification machine is similar to an ultra small jackhammer that fits inside a one-millimeter cannula. The second incision is used to insert an instrument for manipulation of the cataractous natural lens. The instrument inserted in the second incision also has an opening to supply a balanced salt solution to the eye. As the cataractous natural lens is being chopped into small fragments, it is carried away by suction. The BSS replaces the lost fluid in the eye. Today most modern cataract surgeons use a phaco emulsification system that requires a 2.5 millimeter or small incision. To implant a standard cataract lens, the incision size has to be enlarged.

In one embodiment, the method of correcting or improving either a loss of accommodation or lack of accommodation comprises making an incision for access to the anterior chamber of an eye having a length less than 1.5 mm; providing a lens disclosed herein, having a diameter disclosed herein; integrally providing support haptics for anchoring the lens; rolling the lens and the support haptics without exceeding the elastic limit of the material into a rolled package; inserting the rolled package into the anterior chamber of the eye via the incision; unrolling the rolled package internally of the anterior chamber; anchoring the haptics as disclosed herein; and repairing the incision, if necessary, made in the eye.

In other embodiments, the method of correcting or improving either a loss of accommodation or lack of accommodation comprises making an incision for access having a length of less than 1.5 mm; providing a lens formed of an optical grade of an acrylic plastic material having a thickness no greater than 0.25 mm, having a diameter of 11 mm, the lens having a convex first surface and a second surface, wherein the second surface comprises a central disk which is radially surrounded by a series of annular rings found on the central disk in said series of annular rings forming a series of radial steps along said second surface; integrally providing an anchor for the lens support haptics for anchoring the lens; rolling the lens and the support haptics without exceeding the elastic limit of the material into a rolled package; inserting the rolled package into the eye via the incision; unrolling the rolled package; and anchoring the haptics.

As described above, the series of annular rings 14 in the optical portion 48 of the lens 10 perform several functions. The series of annular rings 14 reduce the thickness of the lens 10 thereby reducing the weight of the lens 10. The reduced weight of the optic allows the anchoring means, including, but not limited to, the haptic 18, the plate haptic 22, and/or the anchoring footplate 20, to be thinner and still have the rigidity to correctly position the lens 10 in the eye. Additionally, thin haptics 18, including plate haptics 22, allows the lens 10 to move forward on swell tension of the ciliary body 40 producing accommodation, as shown in FIG. 14.

One surface of the lens 10 is a continuous curve and spherical. Any deviation from the paraxial-ray formulas of the Gauss (Fundamentals of Optics, Jenkins and White, page 149) theory to give an accurate account of image detail is known as spherical aberration. Since a spherical lens produces aberration, many commercial computer programmed lathes cut in a spherical pattern, and the Gaussan formulas are based on spherical lenses, light rays entering the spherical lens focus at a shorter focal length as the distance from the center of the lens increases. This effect is known as spherical aberration and causes glare in the lenses from unfocused light. The series of annular rings 14 are designed to correct for spherical aberration from the continuous curve by adjusting the focal length from each ring 54 to focus at the same point as the prime meridian of the lens. The prime meridian of the lens is the focal length of the lens along the central axis of the lens. Along with the correction for spherical aberration, the lens 10 disclosed herein corrects for coma, which is the second of the monochromatic aberrations of third-order theory. As stated in Fundamentals of Optics, Jenkins and White page 162 and 163, "[i]t derives its name from the comet like appearance of the image of an object point located just off the lens axis." Additionally, the authors state that "[i]t appears the magnification is different in different parts of the lens".

The lens design further claims an extremely thin lens where all the excess materials for the optical portion 48, haptic 18, and anchoring footplates 20 have been removed so that the lens 10 is extremely lightweight and should not cause undue force against the eye. Again, the thinness of the lens 10 reduces the mass of the lens 10 thus allowing it to be folded, rolled or squeezed in order to pass through an incision in the eye of less than 1.5 millimeters.

This present invention may be practiced by modifying the lens disclosed by Worst, in U.S. Pat. Nos. 5,192,319 and 4,215,440. For example, the optical portions of the Worst lens may be modified with the optical surfaces of the present invention.

In other embodiments, the optical portion 48 of the lens 10 has a convex first surface 46. The periphery of the optical portion 48 comprises a parallel lenticular area. The parallel lenticular area is of uniform thickness and is for preventing the phenomenon known as edge effects. A non-optical transition area 52, as shown in FIG. 5, surrounds the parallel lenticular area. In other embodiments, the anchoring portion 50 extends from the transition area 52. In still other embodiments, the anchoring portion 50 comprises a pair of haptics 18 circumvolving the optical portion 48 of the lens 10. Each of the pair of haptics 18 has an outer circumferential haptic edge for biasing against the tissue of the eye.

The central disk 12 and series of annular rings 14 form a series of radial steps across the second surface 44 to maintain a close proximity to the first surface 46. The thickness of the central disk 12 at the apex of the first surface 46 is less than or equal to a predetermined maximum thickness so that the lens 10 may be rolled without exceeding the elastic limit of the lens material. The thickness of the periphery of the central disk 12 is greater than or equal to a predetermined minimum thickness so that the lens 10 will retain its pre-flexed shape subsequent to being rolled.

In certain embodiments, the surfaces of the central disk 12 and each of the annular rings 54 are convex. The thickness of the central disk 12 at the apex of the first surface 46 is less than or equal to the predetermined maximum thickness. The thickness of the periphery of the central disk 12 is greater than or equal to a predetermined minimum thickness.

In other embodiments, the surfaces of the central disk 12 and each of the annular rings 54 are concave. The thickness of the central disk 12 at the periphery of the central disk 12 is less than or equal to the predetermined maximum thickness. The thickness of the lens between the apex of the first surface 46 and the central disk 12 is greater than or equal to a predetermined minimum thickness.

All patents and publications disclosed above are expressly incorporated herein by reference in their entirety.

This invention thus being described, it will be obvious that the same may be varied in many ways. Such variations are not to be regarded as a departure from the spirit and scope of the present invention, and all such modifications as would be obvious to one of ordinary skill in the art are intended to be included within the scope of this invention.

Thus, although there have been described particular embodiments of the present invention of a new and useful Small Incision Lens and Method of Use Thereof, it is not intended that such references be construed as limitations upon the scope of this invention except as set forth in the following claims.

What is claimed is:

1. An intraocular Lens, comprising:
    an optical portion having a first optical surface, wherein the optical portion is constructed of a material which is biologically compatible with a tissue of an eye, the optical portion having a predetermined maximum thickness under which the material may be rolled without exceeding the elastic limit of the material, said optical portion having a predetermined minimum thickness above which the material retains a normal shape, wherein the intraocular lens is capable of deforming for passage through an incision having a length smaller than about 1.5 millimeters so that the intraocular lens is placed into the eye;
    the optical portion having a second optical surface, wherein the second optical surface comprises a central disk which is radially surrounded by a series of annular rings, the central disk and the series of annular rings forming a series of radial steps along the second optical surface so that a focal length from an annular ring is adjusted to focus at a same point as a prime meridian of the lens, wherein the second optical surface and the first optical surface have a minimum separation of 0.025 mm and a maximum separation of 0.45 mm; and
    an anchoring portion attached to the optical portion, wherein the anchoring portion is constructed of a material, which is biologically compatible with a tissue of an eye, wherein the anchoring portion is capable of biasing against a support structure of the eye.

2. The lens of claim 1, wherein the second optical surface and the first optical surface have a minimum separation of 0.025 mm and a maximum separation of 0.065 mm.

3. The lens of claim 1, wherein the first optical surface and the second optical surface are of a predetermined convexity for obtaining a particular focusing power.

4. The lens of claim 1, wherein the first optical surface and the second optical surface are of a predetermined concavity for obtaining a particular focusing power.

5. The lens of claim 1, wherein the first optical surface is of a predetermined convexity for obtaining a particular focusing power, and wherein the second optical surface is of a predetermined concavity for obtaining a particular focusing power.

6. The lens of claim 1, wherein the first optical surface is of a predetermined concavity for obtaining a particular focusing power, and wherein the second optical surface is of a predetermined convexity for obtaining a particular focusing power.

7. The lens of claim 1, wherein the anchoring portion has a thickness of about 10 microns to about 100 microns.

8. The lens of claim 7, wherein the anchoring portion further comprises a plurality of anchoring footplates.

9. The lens of claim 7, wherein the anchoring portion further comprises a plate haptic.

10. The lens of claim 1, wherein the optical portion is constructed of a material having an index of refraction from about 1.4 to about 2.0.

11. An intraocular lens, comprising:
    an optical portion having a first optical surface, wherein the first optical surface is of a predetermined convexity for obtaining a particular focusing power, wherein the optical portion is constructed of a material which is biologically compatible with a tissue of an eye, the optical portion having a predetermined maximum thickness under which the material may be rolled without exceeding the elastic limit of the material, said optical portion having a predetermined minimum thickness above which the material retains a normal shape, wherein the intraocular lens is capable of deforming for passage through an incision having a length smaller than about 1.5 millimeters so that the intraocular lens is placed into the eye;
    the optical portion having a second optical surface, wherein the second optical surface comprises a central disk which is radially surrounded by a series of annular rings, the central disk and the series of annular rings forming a series of radial steps along the second optical surface so that a focal length from an annular ring is adjusted to focus at a same point as a prime meridian of the lens, each annular ring having an outer surface, wherein the central disk is of a predetermined convexity for obtaining a particular focusing power, wherein the second optical surface and the first optical surface have a minimum separation of 0.025 mm and a maximum separation of 0.065 mm; and
    an anchoring portion having a thickness of about 10 microns to about 100 microns attached to the optical portion, wherein the anchoring portion is constructed of a material which is biologically compatible with a tissue of an eye, wherein the anchoring portion is capable of biasing against a support structure of the eye.

12. The lens of claim 11, wherein the intraocular lens is constructed of an acrylic material.

13. The lens of claim 11, wherein the intraocular lens is constructed of a hydrophilic acrylic material.

14. The lens of claim 11, wherein the intraocular lens is constructed of a hydrophobic acrylic material.

15. The lens of claim 11, wherein the intraocular lens is constructed of a polymethylmethacrylate material.

16. The lens of claim 11, wherein the intraocular lens is constructed of a hydrogel material.

17. The lens of claim 11, wherein the optical portion is constructed of a material selected from the group consisting of acrylic, hydrophilic acrylic, hydrophobic acrylic, and hydrogel.

18. The lens of claim 11, wherein the optical portion is constructed of an acrylic material and the anchoring portion is constructed of a polymethylmethacrylate material.

19. The lens of claim 11, wherein the optical portion is constructed of a hydrogel material and the anchoring portion is constructed of a polymethylmethacrylate material.

20. The lens of claim 11, wherein the optical portion is constructed of a hydrogel material and the anchoring portion is constructed of an acrylic material.

21. The lens of claim 11, wherein the outer surface of each annular ring is of a predetermined concavity so that a focal length from the annular ring is adjusted to focus at a same point as a prime meridian of the lens.

22. The lens of claim 11, wherein the outer surface of each annular ring is of a predetermined convexity so that a focal length from the annular ring is adjusted to focus at a same point as a prime meridian of the lens.

23. The lens of claim 11, wherein the anchoring portion further comprises a directional marker.

24. An intraocular lens, comprising:
an optical portion having a first optical surface, wherein the optical portion is constructed of a material which is biologically compatible with a tissue of an eye, wherein the optical portion is constructed of a material having an index of refraction from about 1.4 to about 2.0, wherein the first optical surface is of a predetermined concavity for obtaining a particular focusing power, the optical portion having a predetermined maximum thickness under which the material may be rolled without exceeding the elastic limit of the material, said optical portion having a predetermined minimum thickness above which the material retains a normal shape, wherein the intraocular lens is capable of deforming for passage through an incision having a length smaller than about 1.5 millimeters so that the intraocular lens is placed into the eye;

the optical portion having a second optical surface, wherein the second optical surface comprises a central disk which is radially surrounded by a series of annular rings, the central disk and the series of annular rings forming a series of radial steps along the second optical surface so that a focal length from an annular ring is adjusted to focus at a same point as a prime meridian of the lens, each annular ring having an outer surface, wherein the second optical surface and the first optical surface have a minimum separation of 0.025 mm and a maximum separation of 0.065 mm; and an anchoring portion having a maximum thickness of 100 microns attached to the optical portion, wherein the anchoring portion is constructed of a material which is biologically compatible with a tissue of an eye, wherein the anchoring portion is capable of biasing against a support structure of the eye.

25. The lens of claim 24, wherein the central disk has a predetermined convexity so that a focusing power is obtained and the series of annular rings have a predetermined convexity.

26. The lens of claim 24, wherein the central disk has a predetermined concavity so that a focusing power is obtained and the series of annular rings have a predetermined concavity.

27. The lens of claim 24, wherein the anchoring portion is capable of biasing against an anterior surface of a capsule and a posterior surface of the capsule, wherein biasing produces a minimum radial force on the eye.

28. The lens of claim 24, wherein the anchoring portion is capable of biasing against a zonula and a posterior surface of an iris, wherein biasing produces a minimum radial force on the eye.

29. The lens of claim 28, wherein the anchoring portion is curled so that the anchoring portion is pinched between the zonula and the posterior surface of the iris.

30. The lens of claim 27, wherein the anchoring portion is curled so that the anchoring portion is pinched between the anterior surface of the capsule and the posterior surface of the capsule.

31. The lens of claim 23, wherein the directional marker further comprises an opening.

32. The lens of claim 31, wherein the anchoring portion is arched so that the anchoring portion wedges between the support structures of the eye.

33. The lens of claim 11, wherein the anchoring portion is curved so that the anchoring portion biases between support structures of the eye.

34. The lens of claim 7, wherein the anchoring portion is curved so that the anchoring portion provides and exerts a force against support structures of the eye.

* * * * *